(12) United States Patent
Qu et al.

(10) Patent No.: US 8,697,849 B2
(45) Date of Patent: Apr. 15, 2014

(54) PYRAZOLE COMPOUNDS

(71) Applicant: Eli Lilly and Company, Indianapolis, IN (US)

(72) Inventors: Fucheng Qu, Carmel, IN (US); Nathan Bryan Mantlo, Brownsburg, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/875,314

(22) Filed: May 2, 2013

(65) Prior Publication Data

US 2013/0303471 A1    Nov. 14, 2013

Related U.S. Application Data

(60) Provisional application No. 61/769,221, filed on Feb. 26, 2013, provisional application No. 61/645,101, filed on May 10, 2012.

(51) Int. Cl.
*C07H 17/02* (2006.01)

(52) U.S. Cl.
CPC .................................... *C07H 17/02* (2013.01)
USPC ........................................................ 536/17.4

(58) Field of Classification Search
None
See application file for complete search history.

(56) References Cited

U.S. PATENT DOCUMENTS

| 7,087,579 B2 | 8/2006 | Nishimura et al. |
| 7,115,575 B2 | 10/2006 | Fujikura et al. |
| 7,217,697 B2 | 5/2007 | Shiohara et al. |
| 7,635,684 B2 | 12/2009 | Fushimi et al. |
| 7,655,632 B2 | 2/2010 | Teranishi et al. |
| 7,820,804 B2 | 10/2010 | Brummerhop et al. |
| 2010/0279962 A1 | 11/2010 | Takeuchi et al. |

FOREIGN PATENT DOCUMENTS

| EP | 1544208 A1 | 6/2005 |
| WO | 2005121161 A1 | 12/2005 |
| WO | 2007136116 A2 | 11/2007 |
| WO | 2010095768 A1 | 8/2010 |
| WO | 2011039338 A2 | 4/2011 |

*Primary Examiner* — Eric S Olson
(74) *Attorney, Agent, or Firm* — Nelsen L. Lentz

(57) ABSTRACT

The present invention provides a compound of Formula II:

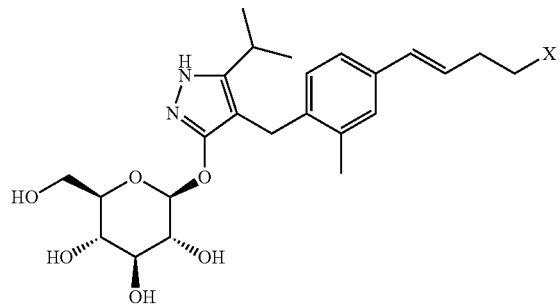

Formula II wherein X represents the following:

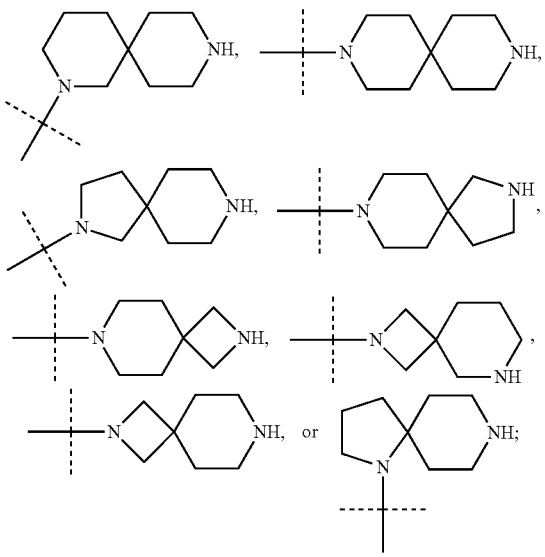

or a pharmaceutically acceptable salt thereof.

8 Claims, No Drawings

PYRAZOLE COMPOUNDS

The present invention relates to novel pyrazole compounds, to pharmaceutical compositions comprising the compounds, to methods of using the compounds to treat physiological disorders, and to intermediates and processes useful in the synthesis of the compounds.

The present invention is in the field of treatment of diabetes and other diseases and disorders associated with hyperglycemia. Diabetes is a group of diseases that is characterized by high levels of blood glucose. It affects approximately 25 million people in the United States and is also the 7$^{th}$ leading cause of death in U.S. according to the 2011 National Diabetes Fact Sheet (U.S. Department of Health and Human Services, Centers for Disease Control and Prevention). Sodium-coupled glucose cotransporters (SGLT's) are one of the transporters known to be responsible for the absorption of carbohydrates, such as glucose. More specifically, SGLT1 is responsible for transport of glucose across the brush border membrane of the small intestine Inhibition of SGLT1 may result in reduced absorption of glucose in the small intestine, thus providing a useful approach to treating diabetes.

U.S. Pat. No. 7,655,632 discloses certain pyrazole derivatives with human SGLT1 inhibitory activity which are further disclosed as useful for the prevention or treatment of a disease associated with hyperglycemia, such as diabetes. In addition, WO 2011/039338 discloses certain pyrazole derivatives with SGLT1/SGLT2 inhibitor activity which are further disclosed as being useful for treatment of bone diseases, such as osteoporosis.

There is a need for alternative drugs and treatment for diabetes. The present invention provides certain novel inhibitors of SGLT1 which may be suitable for the treatment of diabetes.

Accordingly, the present invention provides a compound of Formula II:

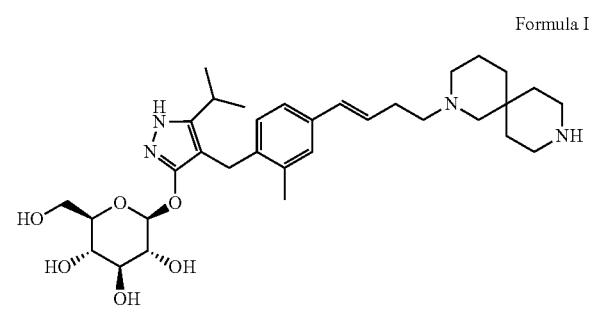

wherein X represents the following:

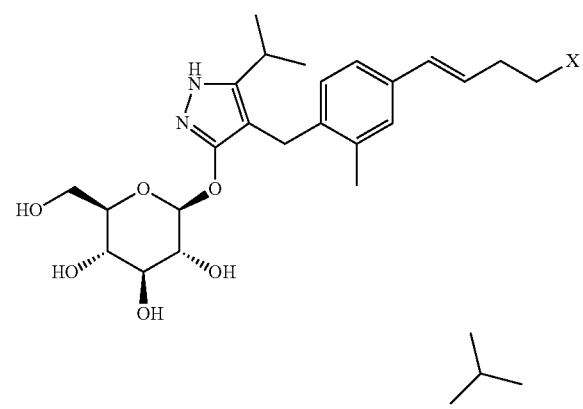

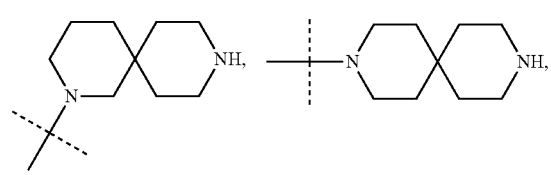

or a pharmaceutically acceptable salt thereof.

The present invention further provides a compound of Formula I:

Formula I

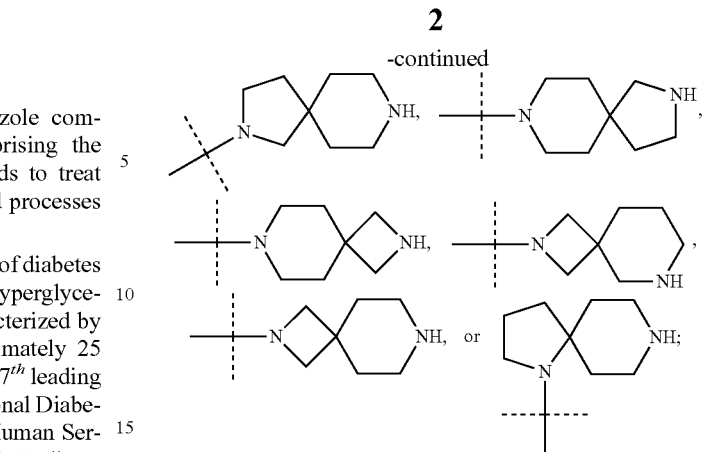

or a pharmaceutically acceptable salt thereof.

The present invention also provides a method of treating diabetes in a patient comprising administering to a patient in need of such treatment an effective amount of a compound of Formulas I or II, or a pharmaceutically acceptable salt thereof. The present invention further provides a method of treating type 1 diabetes in a patient comprising administering to a patient in need of such treatment an effective amount of a compound of Formulas I or II, or a pharmaceutically acceptable salt thereof. In addition, the present invention provides a method of treating type 2 diabetes in a patient comprising administering to a patient in need of such treatment an effective amount of a compound of Formulas I or II, or a pharmaceutically acceptable salt thereof. The present invention also provides a method of treating impaired glucose tolerance (IGT), impaired fasting glucose (IFG), or metabolic syndrome in a patient comprising administering to a patient in need of such treatment an effective amount of a compound of Formulas I or II, or a pharmaceutically acceptable salt thereof.

Furthermore, this invention provides a compound of Formulas I or II, or a pharmaceutically acceptable salt thereof for use in therapy, in particular for the treatment of diabetes. In addition, this invention provides a compound of Formulas I or II, or a pharmaceutically acceptable salt thereof for use in the treatment of type 1 diabetes. In addition, this invention provides a compound of Formulas I or II, or a pharmaceutically acceptable salt thereof for use in the treatment of type 2 diabetes. This invention also provides the use of a compound of Formulas I or II, or a pharmaceutically acceptable salt thereof, for the manufacture of a medicament for the treatment of diabetes. Furthermore, this invention provides the use of a compound of Formulas I or II, or a pharmaceutically acceptable salt thereof, for the manufacture of a medicament for the treatment of type 1 diabetes. This invention also provides the use of a compound of Formulas I or II, or a pharmaceutically acceptable salt thereof, for the manufacture of a medicament for the treatment of type 2 diabetes. The invention also provides the use of a compound of Formulas I or II, or a pharmaceutically acceptable salt thereof, for the manufacture of a medicament for the treatment of IGT, IFG, or metabolic syndrome.

The invention further provides a pharmaceutical composition comprising a compound of Formulas I or II, or a pharmaceutically acceptable salt thereof, in combination with one or more pharmaceutically acceptable carriers, diluents, or excipients. In a particular embodiment, the composition further comprises one or more other therapeutic agents. This invention also encompasses novel intermediates and processes for the synthesis of the compound of Formulas I or II.

As used herein, the terms "treating" or "to treat" includes prohibiting, restraining, slowing, stopping, or reversing the progression or severity of an existing symptom or disorder.

As used herein, the term "patient" refers to a mammal, such as a mouse, guinea pig, rat, dog, or human. It is understood that the preferred patient is a human.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of Formulas I and II are generally effective over a wide dosage range. For example, dosages per day normally fall within the range of about 0.01 to about 30 mg/kg of body weight. In some instances dosage levels below the lower limit of the aforesaid range may be more than adequate, while in other cases still larger doses may be employed without causing any harmful side effect, and therefore the above dosage range is not intended to limit the scope of the invention in any way.

The compounds of the invention are preferably formulated as pharmaceutical compositions administered by any route which makes the compound bioavailable. Most preferably, such compositions are for oral administration. Such pharmaceutical compositions and processes for preparing same are well known in the art. (See, e.g., Remington: The Science and Practice of Pharmacy (D. B. Troy, Editor, 21st Edition., Lippincott, Williams & Wilkins, 2006).

In a further aspect of the invention, the present compounds are administered in combination with one or more therapeutic agents, such as antidiabetic agents. Administration in combination includes simultaneous or sequential administration. In addition, simultaneous administration of the combination can be as a single combination dose or separate doses of each therapeutic agent. Examples of antidiabetic agents include metformin; a DPPIV inhibitor, such as sitagliptin or linagliptin; a sulfonylurea, such as glimepiride; a thiazolidinedione, such as pioglitazone; a basal insulin, such as glargine; a rapid acting insulin, such as HUMALOG or NOVOLOG; A GLP-1 agonist, such as exenatide or liraglutide; an SGLT2 inhibitor, such as dapagliflozin or empagliflozin; a glucagon receptor antagonist, such as LY2409021; and the like.

Compounds of Formulas I and II are prepared as illustrated in both the examples and schemes below. The reagents and starting materials are readily available to one of ordinary skill in the art. All substituents, unless otherwise specified are as previously defined. It is understood that these schemes, preparations, and examples are not intended to be limiting to the scope of the invention in any way.

Examples of resolutions include selective crystallization techniques or chiral chromatography. (See, e.g. J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994). It should be further clear to one of ordinary skill in the art that separation and isolation, by chromatography, chiral chromatography or selective crystallization, of individual diastereomers or geometric isomers of Formula I or II, or individual diastereomers or geometric isomers of intermediates leading to Formula I or II, can occur at any convenient point in the synthesis.

As used herein, "δ" refers to part per million down-field from tetramethylsilane; "min" refers to minute or minutes; "THF" refers to tetrahydrofuran; "MeOH" refers to methanol or methyl alcohol; "HPLC" refers to high-performance liquid chromatography; The term "Ac" refers to an acetyl substituent of the following structure:

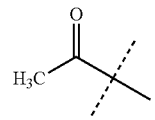

The term "Bz" refers to a benzoyl substituent of the following structure:

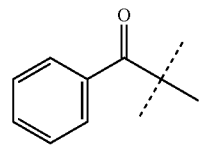

The term "BOC" refers to a t-butyloxycarbonyl protecting group.

Pharmaceutically acceptable salts and common methodology for preparing them are well known in the art. See, e.g., Gould, P. L., "Salt selection for basic drugs," *International Journal of Pharmaceutics,* 33: 201-217 (1986); Bastin et al. "Salt Selection and Optimization Procedures for Pharmaceutical New Chemical Entities," *Organic Process Research and Development,* 4: 427-435 (2000); and S. M. Berge, et al., "Pharmaceutical Salts," Journal of Pharmaceutical Sciences, Vol. 66, No. 1, January 1977. One skilled in the art of synthesis will appreciate that the compounds of Formula I and II, as amines, are organic bases, and that they are readily converted to and isolated as pharmaceutically acceptable salts, such as tartrate or HCl salts, using techniques and conditions well known to one of ordinary skill in the art.

Scheme 1
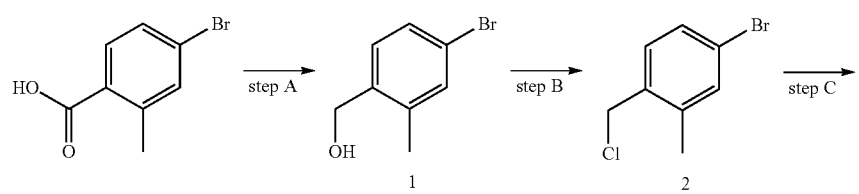
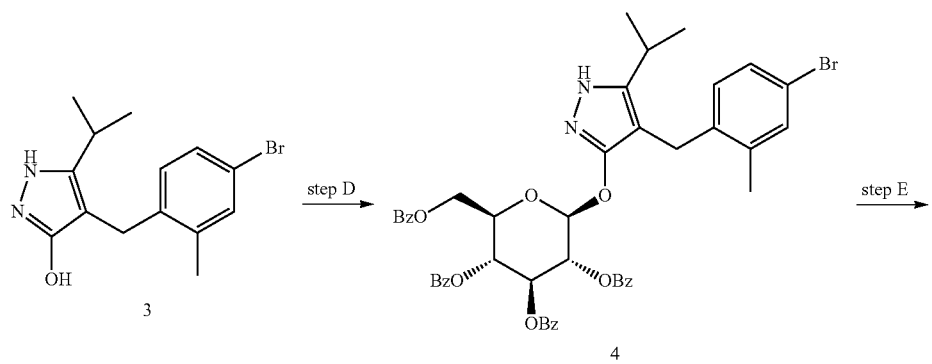
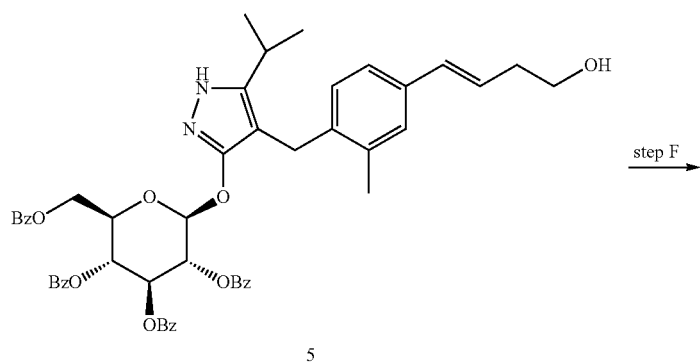
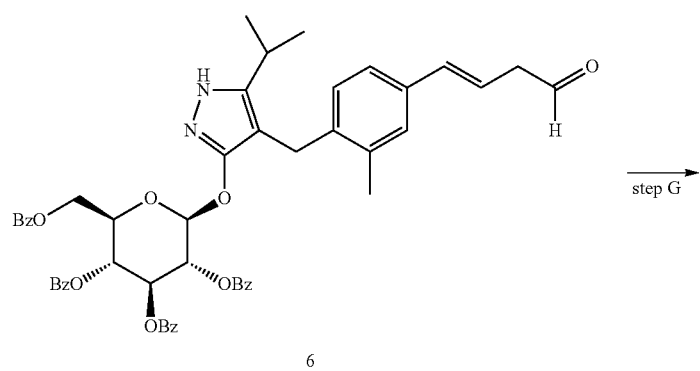

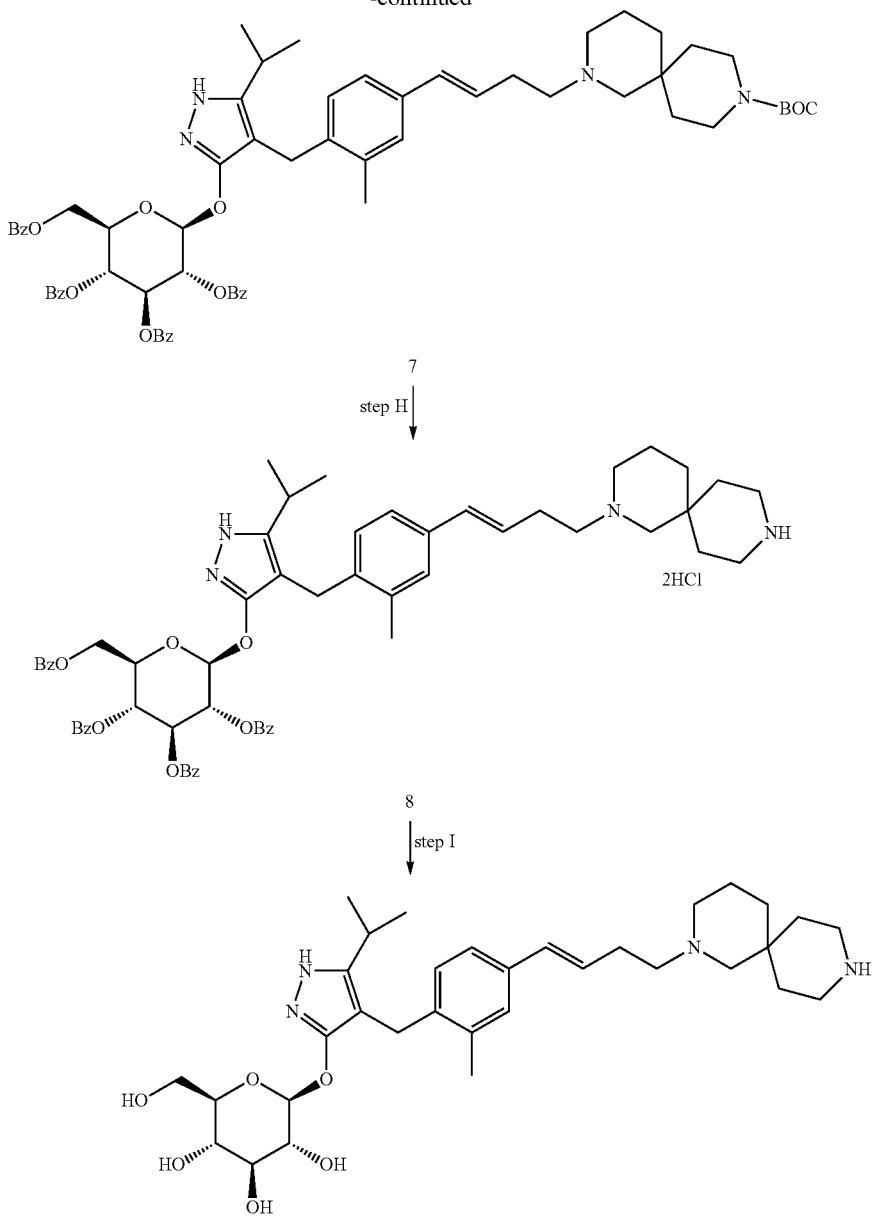

Example 1

PREPARATION 1

Synthesis of (4-bromo-2-methyl-phenyl)methanol

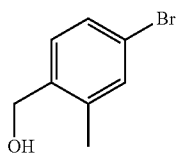

Scheme 1, step A: Add borane-tetrahydrofuran complex (0.2 mol, 200 mL, 1.0 M solution) to a solution of 4-bromo-2-methylbenzoic acid (39 g, 0.18 mol) in tetrahydrofuran (200 mL). After 18 hours at room temperature, remove the solvent under the reduced pressure to give a solid. Purify by flash chromatography to yield the title compound as a white solid (32.9 g, 0.16 mol). $^1$H NMR (CDCl$_3$): δ 1.55 (s, 1H), 2.28 (s, 3H), 4.61 (s, 2H), 7.18-7.29 (m, 3H).

Alternative synthesis of (4-bromo-2-methyl-phenyl)methanol

Borane-dimethyl sulfide complex (2M in THF; 116 mL, 0.232 mol) is added slowly to a solution of 4-bromo-2-methylbenzoic acid (24.3 g, 0.113 mol) in anhydrous tetrahydrofuran (THF, 146 mL) at 3° C. After stirring cold for 10 min the cooling bath is removed and the reaction is allowed to warm slowly to ambient temperature. After 1 hour, the solution is cooled to 5° C., and water (100 mL) is added slowly. Ethyl acetate (100 mL) is added and the phases are separated. The organic layer is washed with saturated aqueous NaHCO$_3$ solution (200 mL) and dried over Na$_2$SO$_4$. Filtration and concentration under reduced pressure gives a residue which is purified by filtration through a short pad of silica eluting with 15% ethyl acetate/iso-hexane to give the title compound (20.7 g, 91.2% yield). MS (m/z): 183/185 (M+1-18).

PREPARATION 2

Synthesis of 4-bromo-1-chloromethyl-2-methyl-benzene

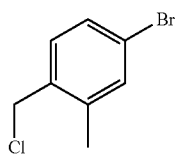

Scheme 1, step B: Add thionyl chloride (14.31 mL, 0.2 mol,) to a solution of (4-bromo-2-methyl-phenyl)methanol (32.9 g, 0.16 mol) in dichloromethane (200 mL) and dimethylformamide (0.025 mol, 2.0 mL) at 0° C. After 1 hour at room temperature pour the mixture into ice-water (100 g), extract with dichloromethane (300 mL), wash extract with 5% aq. sodium bicarbonate (30 mL) and brine (200 mL), dry over sodium sulfate, and concentrate under reduced pressure to give the crude title compound as a white solid (35.0 g, 0.16 mol). The material is used for the next step of reaction without further purification. $^1$H NMR (CDCl$_3$): δ 2.38 (s, 3H), 4.52 (s, 2H), 7.13-7.35 (m, 3H).

Alternative synthesis of 4-bromo-1-chloromethyl-2-methyl-benzene

Methanesulfonyl chloride (6.83 mL, 88.3 mmol) is added slowly to a solution of (4-bromo-2-methyl-phenyl)methanol (16.14 g, 80.27 mmol) and triethylamine (16.78 mL; 120.4 mmol) in dichloromethane (80.7 mL) cooled in ice/water. The mixture is allowed to slowly warm to ambient temperature and is stirred for 16 hours. Further methanesulfonyl chloride (1.24 mL; 16.1 mmol) is added and the mixture is stirred at ambient temperature for 2 hours. Water (80 mL) is added and the phases are separated. The organic layer is washed with hydrochloric acid (1N; 80 mL) then saturated aqueous sodium hydrogen carbonate solution (80 mL), then water (80 mL), and is dried over Na$_2$SO$_4$. Filtration and concentration under reduced pressure gives a residue which is purified by flash chromatography (eluting with hexane) to give the title compound (14.2 g; 80.5% yield). $^1$H NMR (300.11 MHz, CDCl$_3$): δ 7.36-7.30 (m, 2H), 7.18 (d, J=8.1 Hz, 1H), 4.55 (s, 2H), 2.41 (s, 3H).

PREPARATION 3

Synthesis of 4-[(4-bromo-2-methyl-phenyl)methyl]-5-isopropyl-1H-pyrazol-3-ol

Scheme 1, step C: Add sodium hydride (8.29 g, 0.21 mol, 60% dispersion in oil) to a solution of methyl 4-methyl-3-oxovalerate (27.1 mL, 0.19 mol) in tetrahydrofuran at 0° C. After 30 min at room temperature, add a solution of 4-bromo-1-chloromethyl-2-methyl-benzene (35.0 g, 0.16 mol) in tetrahydrofuran (50 mL). Heat the resulting mixture at 70° C. overnight (18 hours). Add 1.0 M HCl (20 mL) to quench the reaction. Extract with ethyl acetate (200 mL), wash extract with water (200 mL) and brine (200 mL), dry over Na$_2$SO$_4$, filter and concentrate under reduced pressure. Dissolve the resulting residue in toluene (200 mL) and add hydrazine monohydrate (23.3 mL, 0.48 mol). Heat the mixture at 120° C. for 2 hours with a Dean-Stark apparatus to remove water. Cool and remove the solvent under the reduced pressure, dissolve the residue with dichloromethane (50 mL) and methanol (50 mL). Pour this solution slowly to a beaker with water (250 mL). Collect the resulting precipitated product by vacuum filtration. Dry in vacuo in an oven overnight at 40° C. to yield the title compound as a solid (48.0 g, 0.16 mol). MS (m/z): 311.0 (M+1), 309.0 (M−1).

Alternative synthesis of 4-[(4-bromo-2-methyl-phenyl)methyl]-5-isopropyl-1H-pyrazol-3-ol A solution of 4-bromo-1-chloromethyl-2-methyl-benzene (13.16 g, 59.95 mmoles) in acetonitrile (65.8 mL) is prepared. Potassium carbonate (24.86 g, 179.9 mmol), potassium iodide (11.94 g, 71.94 mmol) and methyl 4-methyl-3-oxovalerate (8.96 mL; 62.95 mmol) are added. The resulting mixture is stirred at ambient temperature for 20 hours. Hydrochloric acid (2N) is added to give pH 3. The solution is extracted with ethyl acetate (100 ml), the organic phase is washed with brine (100 ml) and dried over Na$_2$SO$_4$. The mixture is filtered and concentrated under reduced pressure. The residue is dissolved in toluene (65.8 mL) and hydrazine monohydrate (13.7 mL, 0.180 mol) is added. The resulting mixture is heated to reflux and water is removed using a Dean and Stark apparatus. After 3 hours the mixture is cooled to 90° C. and additional hydrazine monohydrate (13.7 mL; 0.180 mol) is added and the mixture is heated to reflux for 1 hour. The mixture is cooled and concentrated under reduced pressure. The resulting solid is triturated with water (200 mL), filtered and dried in a vacuum oven over P$_2$O$_5$ at 60° C. The solid is triturated in iso-hexane (200 mL) and filtered to give the title compound (14.3 g; 77.1% yield). MS (m/z): 309/311 (M+1).

PREPARATION 4

Synthesis of 4-(4-bromo-2-methylbenzyl)-5-(propan-2-yl)-1H-pyrazol-3-yl 2,3,4,6-tetra-O-benzoyl-beta-D-glucopyranoside

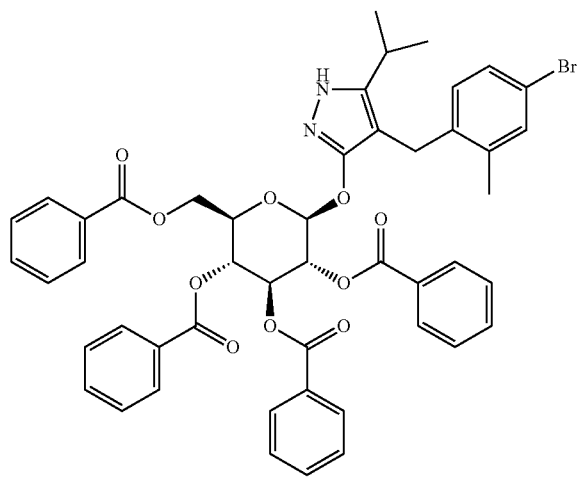 [SMILES: Cc1cc(Br)ccc1Cc1c(O[C@@H]2O[C@H](COC(=O)c3ccccc3)[C@@H](OC(=O)c3ccccc3)[C@H](OC(=O)c3ccccc3)[C@H]2OC(=O)c2ccccc2)n[nH]c1C(C)C]

Scheme 1, step D: To a 1 L flask, add 4-[(4-bromo-2-methyl-phenyl)methyl]-5-isopropyl-1H-pyrazol-3-ol (20 g, 64.7 mmol), alpha-D-glucopyranosyl bromide tetrabenzoate (50 g, 76 mmol), benzyltributylammonium chloride (6 g, 19.4 mmol), dichloromethane (500 mL), potassium carbonate (44.7 g, 323 mmol) and water (100 mL). Stir the reaction mixture overnight at room temperature. Extract with dichloromethane (500 mL). Wash extract with water (300 mL) and brine (500 mL). Dry organic phase over sodium sulfate, filter, and concentrate under reduced pressure. Purify the residue by flash chromatography to yield the title compound (37 g, 64 mmol). MS (m/z): 889.2 (M+1), 887.2 (M−1).

PREPARATION 5

Synthesis of 4-{4-[(1E)-4-hydroxybut-1-en-1-yl]-2-methylbenzyl}-5-(propan-2-yl)-1H-pyrazol-3-yl 2,3,4,6-tetra-O-benzoyl-beta-D-glucopyranoside

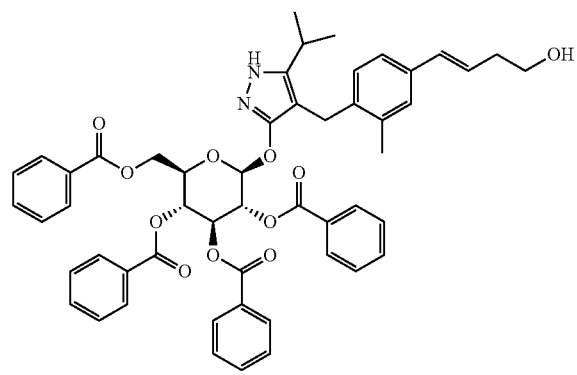 [SMILES: Cc1cc(/C=C/CCO)ccc1Cc1c(O[C@@H]2O[C@H](COC(=O)c3ccccc3)[C@@H](OC(=O)c3ccccc3)[C@H](OC(=O)c3ccccc3)[C@H]2OC(=O)c2ccccc2)n[nH]c1C(C)C]

Scheme 1, step E: Add 3-buten-1-ol (0.58 mL, 6.8 mmol) to a solution of 4-(4-bromo-2-methylbenzyl)-5-(propan-2-yl)-1H-pyrazol-3-yl2,3,4,6-tetra-O-benzoyl-beta-D-glucopyranoside (3 g, 3.4 mmol) in acetonitrile (30 mL) and triethylamine (20 mL). Degas the solution with nitrogen over 10 minutes. Add tri-o-tolylphosphine (205 mg, 0.67 mmol) and palladium acetate (76 mg, 0.34 mmol). Reflux at 90° C. for 2 hours. Cool to room temperature and concentrate to remove the solvent under the reduced pressure. Purify the residue by flash chromatography to yield the title compound (2.1 g, 2.4 mmol). MS (m/z): 878.4 (M+1).

PREPARATION 6

Synthesis of 4-{4-[(1E)-4-oxybut-1-en-1-yl]-2-methylbenzyl}-5-(propan-2-yl)-1H-pyrazol-3-yl 2,3,4,6-tetra-O-benzoyl-beta-D-glucopyranoside

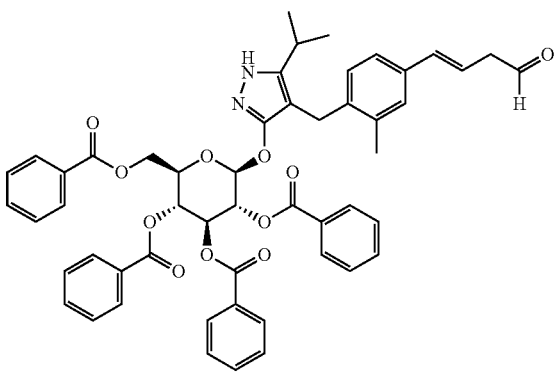 [SMILES: Cc1cc(/C=C/CC=O)ccc1Cc1c(O[C@@H]2O[C@H](COC(=O)c3ccccc3)[C@@H](OC(=O)c3ccccc3)[C@H](OC(=O)c3ccccc3)[C@H]2OC(=O)c2ccccc2)n[nH]c1C(C)C]

Scheme 1, step F: Add 3,3,3-triacetoxy-3-iodophthalide (134 mg, 0.96 mmol) to a solution of 4-{4-[(1E)-4-hydroxybut-1-en-1-yl]-2-methylbenzyl}-5-(propan-2-yl)-1H-pyrazol-3-yl2,3,4,6-tetra-O-benzoyl-beta-D-glucopyranoside (280 mg, 0.32 mmol) and sodium bicarbonate (133.8 mg, 1.6 mmol) in dichloromethane (20 mL) at 0° C. After 15 minutes at room temperature, quench the reaction with saturated aqueous sodium thiosulfate (10 mL). Extract with dichloromethane (30 mL). Wash extract with water (30 mL) and brine (40 mL). Dry organic phase over sodium sulfate, filter, and concentrate under reduced pressure. Purify the resulting residue by flash chromatography to yield the title compound (270 mg, 0.31 mmol). MS (m/z): 876.5 (M+1), 874.5 (M−1).

PREPARATION 7

Synthesis of tert-butyl 2-{(3E)-4-[3-methyl-4-({5-(propan-2-yl)-3-[(2,3,4,6-tetra-O-benzoyl-beta-D-glucopyranosyl)oxy]-1H-pyrazol-4-yl}methyl)phenyl]but-3-en-1-yl}-2,9-diazaspiro[5.5]undecane-9-carboxylate

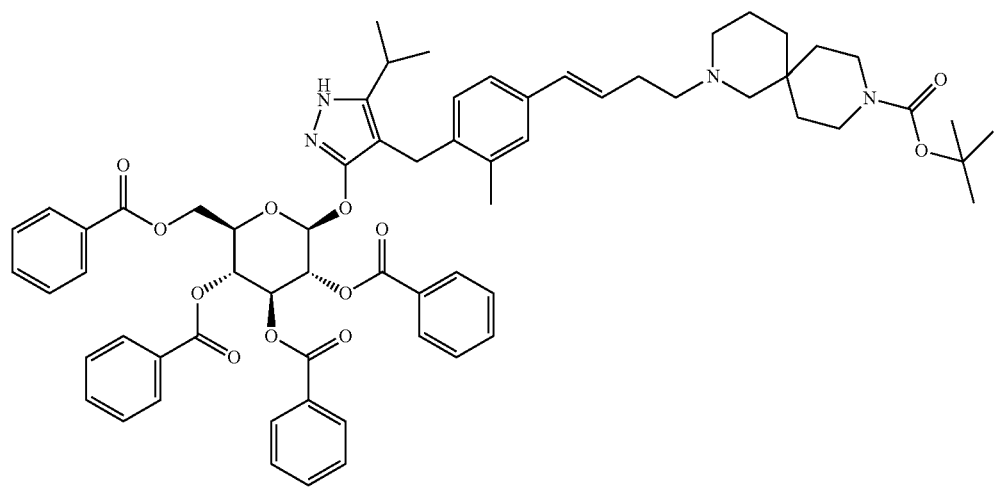 [SMILES: Cc1cc(/C=C/CCN2CCCC3(CCN(C(=O)OC(C)(C)C)CC3)C2)ccc1Cc1c(O[C@@H]2O[C@H](COC(=O)c3ccccc3)[C@@H](OC(=O)c3ccccc3)[C@H](OC(=O)c3ccccc3)[C@H]2OC(=O)c2ccccc2)n[nH]c1C(C)C]

Scheme 1, step G: Add sodium triacetoxyborohydride (98 mg, 0.46 mmol) to a solution of 4-{4-[(1E)-4-oxybut-1-en-1-yl]-2-methylbenzyl}-5-(propan-2-yl)-1H-pyrazol-3-yl2,3,4,6-tetra-O-benzoyl-beta-D-glucopyranoside (270 mg, 0.31 mmol) and tert-butyl 2,9-diazaspiro[5.5]undecane-9-carboxylate hydrochloride (179 mg, 0.62 mmol) in 1,2-dichloroethane (5 mL). After 30 minutes at room temperature, quench the reaction with saturated aqueous sodium bicarbonate (10 mL). Extract with dichloromethane (30 mL). Wash extract with water (30 mL) and brine (40 mL), dry organic phase over sodium sulfate, filter and concentrate under reduced pressure. Purify the resulting residue by flash chromatography to yield the title compound (275 mg, 0.25 mmol).

MS (m/z): 1115.6 (M+1).

PREPARATION 8

Synthesis of 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-benzoyl-beta-D-glucopyranoside dihydrochloride

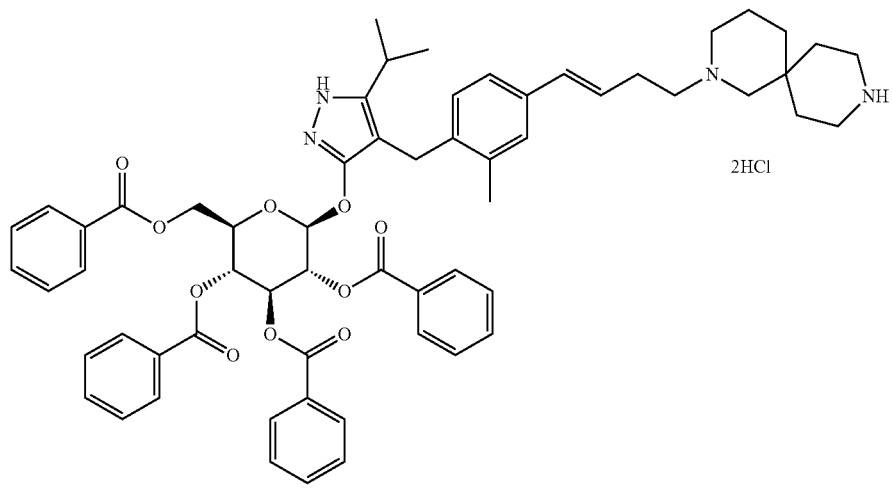 [SMILES: Cc1cc(/C=C/CCN2CCCC3(CCNCC3)C2)ccc1Cc1c(O[C@@H]2O[C@H](COC(=O)c3ccccc3)[C@@H](OC(=O)c3ccccc3)[C@H](OC(=O)c3ccccc3)[C@H]2OC(=O)c2ccccc2)n[nH]c1C(C)C]

Scheme 1, step H: Add hydrogen chloride (4.0 M solution in 1,4-dioxane, 0.6 mL, 2.4 mmol) to a solution of tert-butyl 2-{(3E)-4-[3-methyl-4-({5-(propan-2-yl)-3-[(2,3,4,6-tetra-O-benzoyl-beta-D-glucopyranosyl)oxy]-1H-pyrazol-4-yl}methyl)phenyl]but-3-en-1-yl}-2,9-diazaspiro[5.5]undecane-9-carboxylate (275 mg, 0.25 mmol) in dichloromethane (5 mL). After overnight (18 hours) at room temperature, concentrate to remove the solvent under reduced pressure to yield the title compound as a solid (258 mg, 0.24 mmol). MS (m/z): 1015.6 (M+1).

EXAMPLE 1

Synthesis of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside

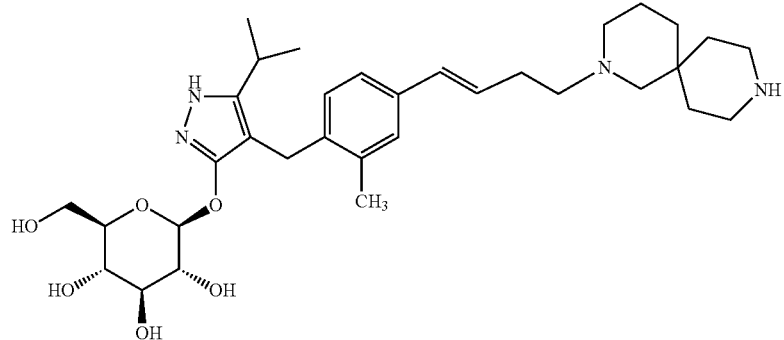 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

Scheme 1, step I: Add sodium hydroxide (0.5 mL, 0.5 mmol, 1.0 M solution) to a solution of 4-{4-[(1E)-4-(2,9-diazaspiro[5.5]undec-2-yl)but-1-en-1-yl]-2-methylbenzyl}-5-(propan-2-yl)-1H-pyrazol-3-yl2,3,4,6-tetra-O-benzoyl-beta-D-glucopyranoside dihydrochloride (258 mg, 0.24 mmol) in methanol (2 mL). After 2 hours at 40° C., concentrate to remove the solvent under reduced pressure to give a residue, which is purified by preparative HPLC method: high pH, 25% B for 4 min, 25-40 B % for 4 min @ 85 mL/min using a 30×75 mm, 5 um C18XBridge ODB column, solvent A—$H_2O$ w $NH_4HCO_3$ @ pH 10, solvent B-MeCN to yield the title compound as a solid (46 mg, 0.08 mmol). MS (m/z): 598.8 (M+1), 596.8 (M−1).

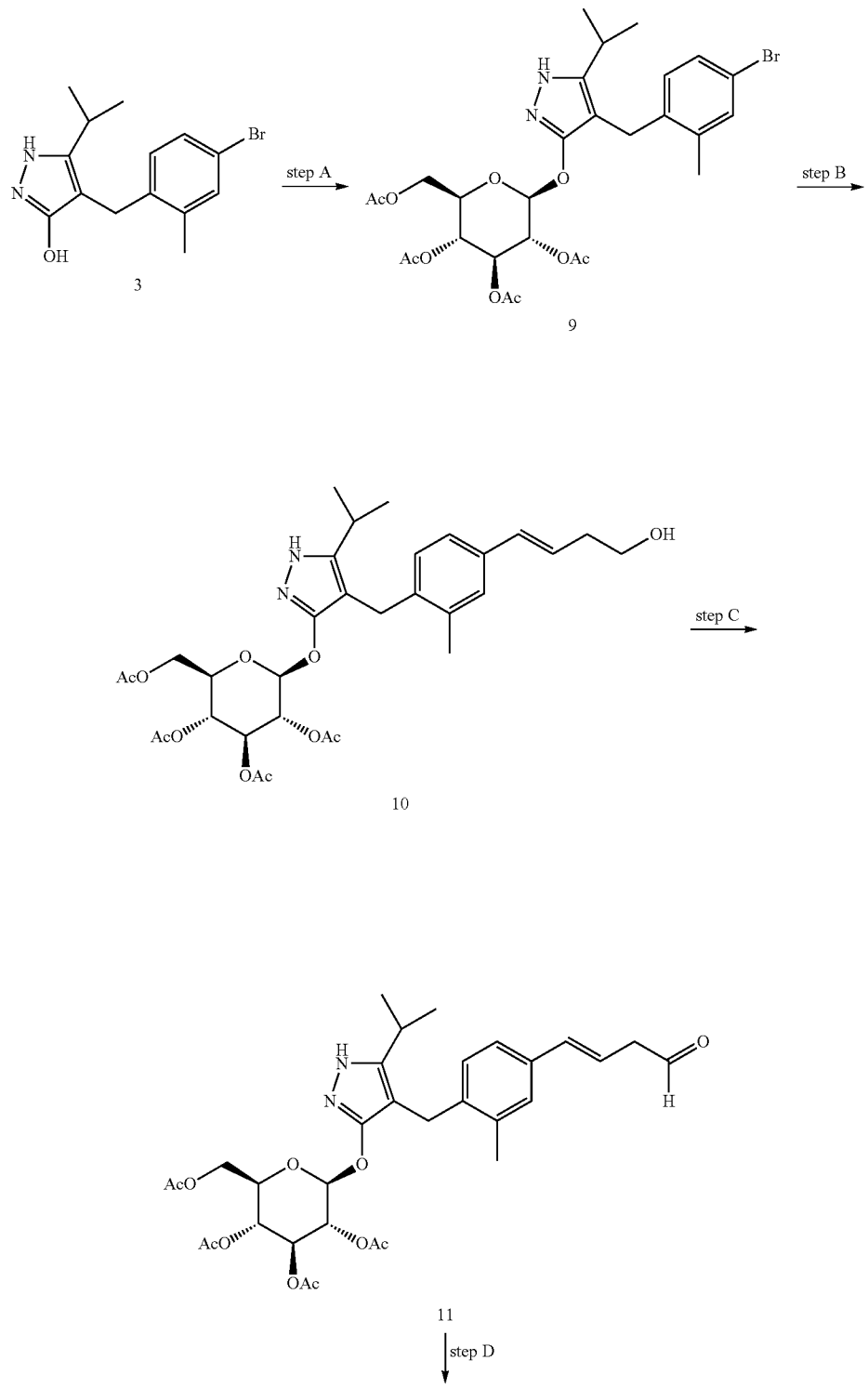

-continued
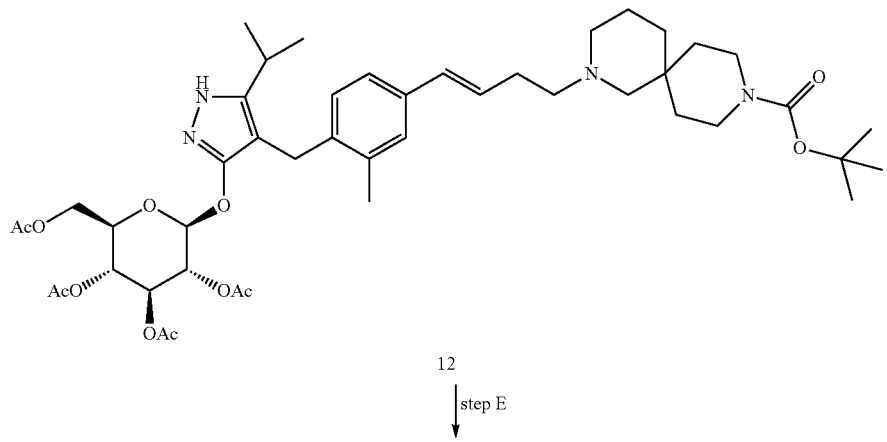
12 ↓ step E
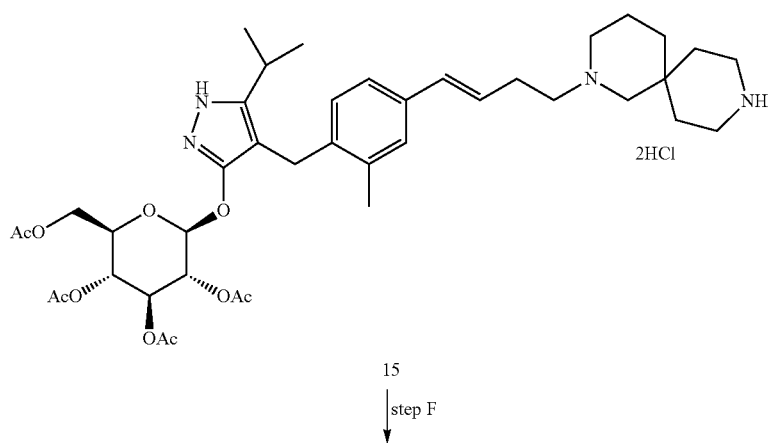
15 ↓ step F
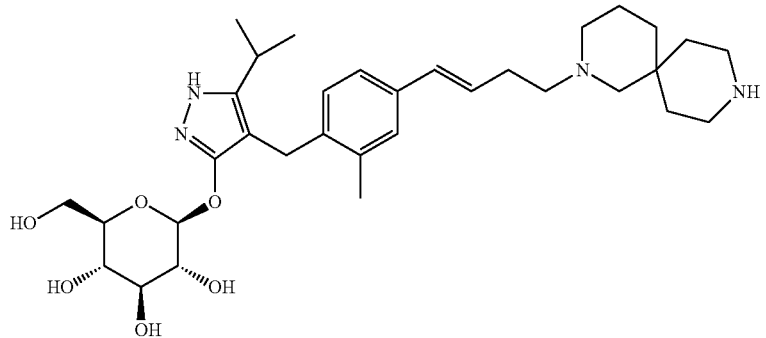
Example 1

PREPARATION 9

Synthesis of 4-(4-bromo-2-methylbenzyl)-5-(propan-2-yl)-1H-pyrazol-3-yl 2,3,4,6-tetra-O-acetyl-beta-D-glucopyranoside

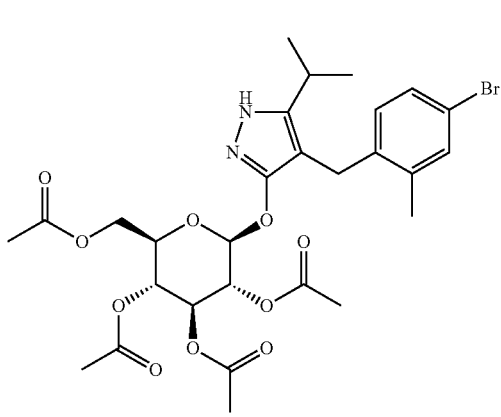 [SMILES: CC(=O)OC[C@H]1O[C@@H](Oc2n[nH]c(C(C)C)c2Cc2ccc(Br)cc2C)[C@H](OC(C)=O)[C@@H](OC(C)=O)[C@@H]1OC(C)=O]

Scheme 2, step A: To a 1 L flask, add 4-[(4-bromo-2-methyl-phenyl)methyl]-5-isopropyl-1H-pyrazol-3-ol (24 g, 77.6 mmol), 2,3,4,6-tetra-O-acetyl-alpha-D-glucopyranosyl bromide (50.4 g, 116 mmol), benzyltributylammonium chloride (5 g, 15.5 mmol), dichloromethane (250 mL), potassium carbonate (32 g, 323 mmol) and water (120 mL). Stir the reaction mixture overnight at room temperature. Extract with dichloromethane (450 mL). Wash extract with water (300 mL) and brine (500 mL). Dry organic phase over sodium sulfate, filter, and concentrate under reduced pressure. Purify the resulting residue by flash chromatography to yield the title compound (36.5 g, 57 mmol). MS (m/z): 638.5 (M+1), 636.5 (M−1).

Alternative synthesis of 4-(4-bromo-2-methylbenzyl)-5-(propan-2-yl)-1H-pyrazol-3-yl 2,3,4,6-tetra-O-acetyl-beta-D-glucopyranoside Reagents 4[(4-bromo-2-methyl-phenyl)methyl]-5-isopropyl-1H-pyrazol-3-ol (24.0 g, 77.6 mmol), 2,3,4,6-tetra-O-acetyl-alpha-D-glucopyranosyl bromide (50.4 g, 116 mmol), benzyltributylammonium chloride (4.94 g, 15.52 mmol), potassium carbonate (32.18 g, 232.9 mmol), dichloromethane (250 mL) and water (120 mL) are combined and the mixture is stirred at ambient temperature for 18 hours. The mixture is partitioned between dichloromethane (250 mL) and water (250 mL). The organic phase is washed with brine (250 mL), dried over Na$_2$SO$_4$, filtered, and concentrated under reduced pressure. The resulting residue is purified by flash chromatography (eluting with 10% ethyl acetate in dichloromethane to 70% ethyl acetate in dichloromethane) to give the title compound (36.5 g, 74% yield). MS (m/z): 639/641 (M+1).

PREPARATION 10

Synthesis of 4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside

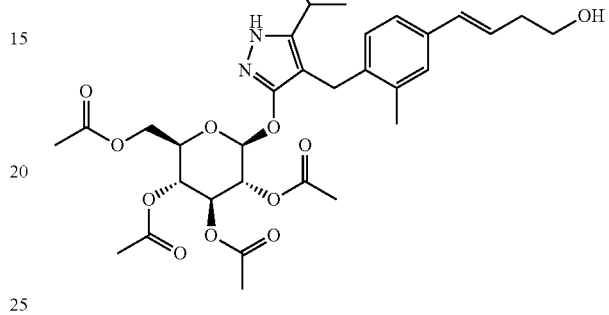

Scheme 2, step B: Add 3-buten-1-ol (6.1 mL, 70 mmol) to a solution of 4-(4-bromo-2-methylbenzyl)-5-(propan-2-yl)-1H-pyrazol-3-yl 2,3,4,6-tetra-O-acetyl-beta-D-glucopyranoside (15 g, 23.5 mmol) in acetonitrile (200 mL) and triethylamine (50 mL). Degas the solution with nitrogen over 10 minutes. Add tri-o-tolylphosphine (1.43 g, 4.7 mmol) and palladium acetate (526 mg, 2.35 mmol). After refluxing at 90° C. for 2 hours, cool, and concentrate to remove the solvent under the reduced pressure. Purify the resulting residue by flash chromatography to yield the title compound (7.5 g, 11.9 mmol).
MS (m/z): 631.2 (M+1), 629.2 (M−1).

PREPARATION 11

Synthesis of 4-{4-[(1E)-4-oxybut-1-en-1-yl]-2-methylbenzyl}-5-(propan-2-yl)-1H-pyrazol-3-yl 2,3,4,6-tetra-O-acetyl-beta-D-glucopyranoside

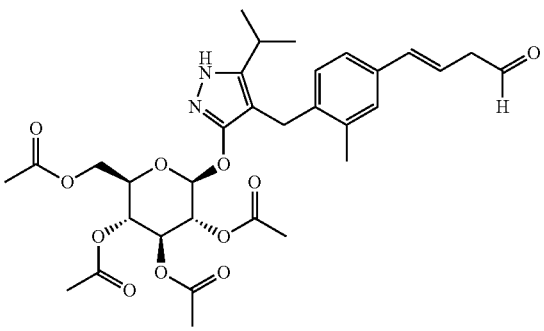 [SMILES: CC(=O)OC[C@H]1O[C@@H](Oc2n[nH]c(C(C)C)c2Cc2ccc(/C=C/CC=O)cc2C)[C@H](OC(C)=O)[C@@H](OC(C)=O)[C@@H]1OC(C)=O]

Scheme 2, step C: Add 3,3,3-triacetoxy-3-iodophthalide (2.1 g, 4.76 mmol) to a solution of 4-{4-[(1E)-4-hydroxybut-1-en-1-yl]-2-methylbenzyl}-5-(propan-2-yl)-1H-pyrazol-3-yl 2,3,4,6-tetra-O-acetyl-beta-D-glucopyranoside (1.5 g, 2.38 mmol) and sodium bicarbonate (2 g, 23.8 mmol) in dichloromethane (50 mL) at 0° C. After 15 minutes at room temperature, quench the reaction with saturated aqueous sodium thiosulfate (10 mL). Extract with dichloromethane (30 mL), wash extract with water (30 mL) and brine (40 mL). Dry organic phase over sodium sulfate, filter, and concentrate under reduced pressure. Purify the resulting residue by flash chromatography to yield the title compound (0.95 g, 1.51 mmol). MS (m/z): 628.8 (M+1), 626.8 (M−1).

PREPARATION 12

Synthesis of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate

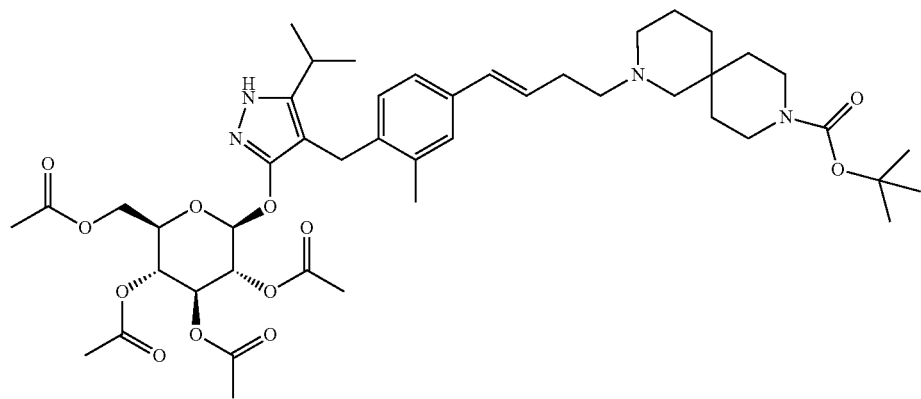 [SMILES: CC(=O)OC[C@H]1O[C@@H](Oc2n[nH]c(C(C)C)c2Cc2ccc(/C=C/CCN3CCCC4(CCN(C(=O)OC(C)(C)C)CC4)C3)cc2C)[C@H](OC(C)=O)[C@@H](OC(C)=O)[C@@H]1OC(C)=O]

Scheme 2, Step D: Add sodium triacetoxyborohydride (303 mg, 1.4 mmol) to a solution of 4-{4-[(1E)-4-oxybut-1-en-1-yl]-2-methylbenzyl}-5-(propan-2-yl)-1H-pyrazol-3-yl 2,3,4,6-tetra-O-acetyl-beta-D-glucopyranoside (600 mg, 0.95 mmol) and tert-butyl 2,9-diazaspiro[5.5]undecane-9-carboxylate hydrochloride (333 mg, 1.2 mmol) in 1,2-dichloroethane (30 mL). After 30 minutes at room temperature, quench the reaction with saturated aqueous sodium bicarbonate (15 mL). Extract with dichloromethane (60 mL). Wash extract with water (30 mL) and brine (60 mL). Dry organic phase over sodium sulfate, filter, and concentrate under reduced pressure. Purify the resulting residue by flash chromatography to yield the title compound (500 mg, 0.58 mmol).
MS (m/z): 866.8, 867.8 (M+1), 864.8, 865.8 (M−1).

PREPARATION 13

Synthesis of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,8-diazaspiro[4.5]decane-8-carboxylate

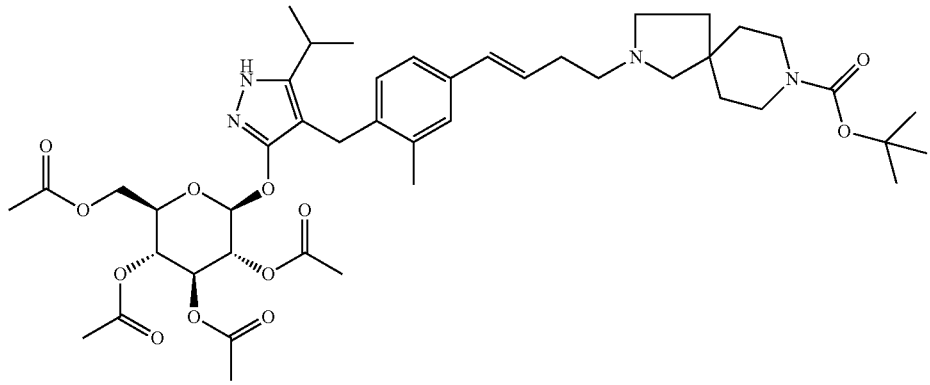 [SMILES: CC(=O)OC[C@H]1O[C@@H](Oc2n[nH]c(C(C)C)c2Cc2ccc(/C=C/CCN3CCC4(CCN(C(=O)OC(C)(C)C)CC4)C3)cc2C)[C@H](OC(C)=O)[C@@H](OC(C)=O)[C@@H]1OC(C)=O]

The title compound is prepared essentially by the method of Preparation 12.

MS (m/z): 852.8, 853.6 (M+1), 850.8, 851.6 (M−1).

PREPARATION 14

Synthesis of tert-butyl 9-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-3,9-diazaspiro[5.5]undecane-3-carboxylate

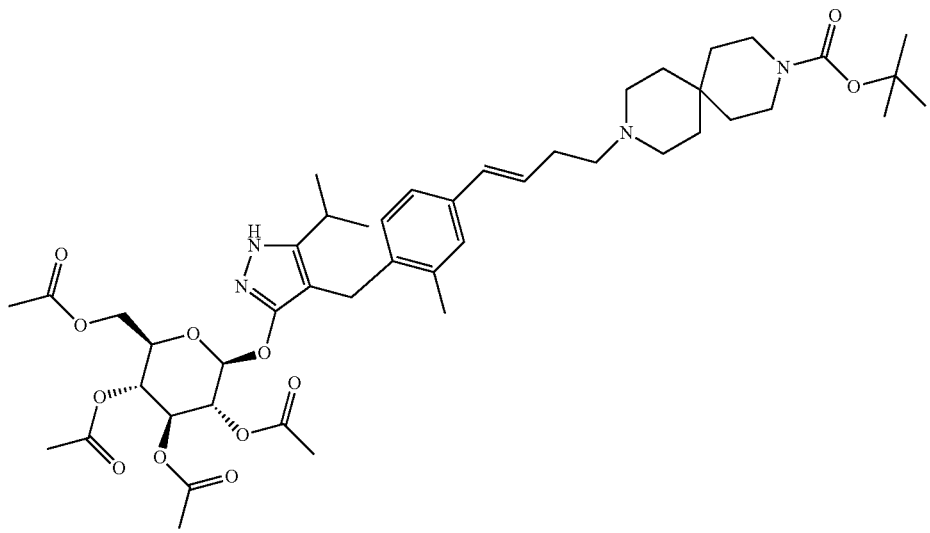 [SMILES: CC(=O)OC[C@H]1O[C@@H](Oc2n[nH]c(C(C)C)c2Cc2ccc(/C=C/CCN3CCC4(CC3)CCN(C(=O)OC(C)(C)C)CC4)cc2C)[C@H](OC(C)=O)[C@@H](OC(C)=O)[C@@H]1OC(C)=O]

The title compound is prepared essentially by the method of Preparation 12.

MS (m/z): 866.8, 867.6 (M+1), 864.8, 865.6 (M−1).

PREPARATION 15

Synthesis of 4-{4-[(1E)-4-(2,9-diazaspiro[5.5]undec-2-yl)but-1-en-1-yl]-2-methylbenzyl}-5-(propan-2-yl)-1H-pyrazol-3-yl2,3,4,6-tetra-O-acetyl-beta-D-glucopyranoside dihydrochloride

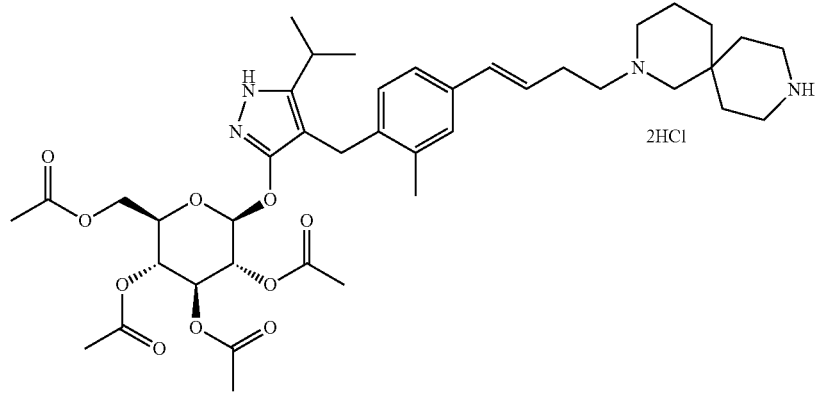 [SMILES: CC(=O)OC[C@H]1O[C@@H](Oc2n[nH]c(C(C)C)c2Cc2ccc(/C=C/CCN3CCCC4(CCNCC4)C3)cc2C)[C@H](OC(C)=O)[C@@H](OC(C)=O)[C@@H]1OC(C)=O]

Scheme 2, step E: Add hydrogen chloride (4.0 M solution in 1,4-dioxane, 1.5 mL, 5.8 mmol) to a solution of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,9-diazaspiro[5.5]undecane-9-carboxylate (500 mg, 0.58 mmol) in dichloromethane (20 mL). After 2 hours at room temperature, concentrate to remove the solvent under reduced pressure to yield the title compound as a solid (480 mg, 0.57 mmol).

MS (m/z): 767.4 (M+1).

PREPARATION 16

Synthesis of 4-{4-[(1E)-4-(2,8-diazaspiro[4.5]dec-2-yl)but-1-en-1-yl]-2-methylbenzyl}-5-(propan-2-yl)-1H-pyrazol-3-yl2,3,4,6-tetra-O-acetyl-beta-D-glucopyranoside dihydrochloride

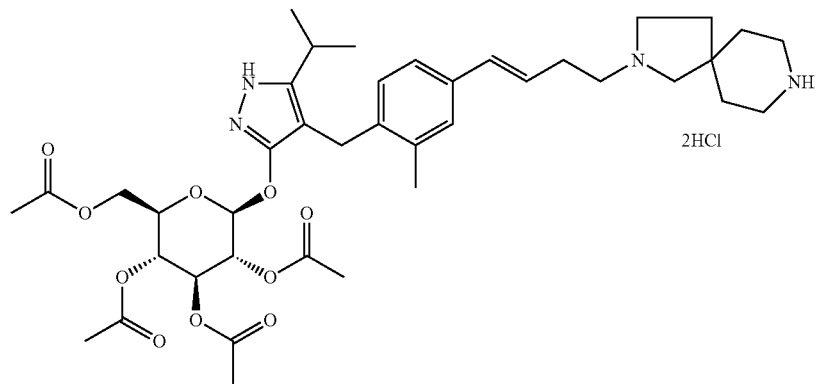 [SMILES: CC(=O)OC[C@H]1O[C@@H](Oc2n[nH]c(C(C)C)c2Cc2ccc(/C=C/CCN3CCC4(CCNCC4)C3)cc2C)[C@H](OC(C)=O)[C@@H](OC(C)=O)[C@@H]1OC(C)=O]

The title compound is prepared essentially by the method of Preparation 15.

MS (m/z): 752.8, 753.8 (M+1), 750.8 (M−1).

First Alternative Synthesis of Example 1

First alternative synthesis of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside

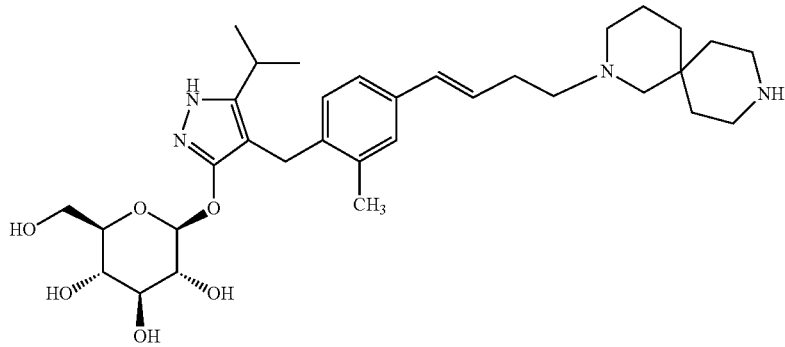 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

Scheme 2, step F: Add methanol (5 mL), triethylamine (3 mL), and water (3 mL) to 4-{4-[(1E)-4-(2,9-diazaspiro[5.5]undec-2-yl)but-1-en-1-yl]-2-methylbenzyl}-5-(propan-2-yl)-1H-pyrazol-3-yl 2,3,4,6-tetra-O-acetyl-beta-D-glucopyranoside dihydrochloride (480 mg, 0.24 mmol). After 18 hours (overnight) at room temperature, concentrate to dryness under reduced pressure. Purify the resulting residue by preparative HPLC method: high pH, 25% B for 4 min, 25-40 B % for 4 min @ 85 mL/min using a 30×75 mm, 5 um C18XBridge ODB column, solvent A—$H_2O$ w $NH_4HCO_3$ @ pH 10, solvent B-MeCN to yield the title compound as a solid (50 mg, 0.08 mmol).

MS (m/z): 598.8 (M+1), 596.8 (M−1). $^1$H NMR (400.31 MHz, $CD_3OD$): δ 7.11 (d, J=1.3 Hz, 1H), 7.04 (dd, J=1.3, 8.0 Hz, 1H), 6.87 (d, J=8.0 Hz, 1H), 6.36 (d, J=15.8 Hz, 1H), 6.16 (dt, J=15.8, 6.3 Hz, 1H), 5.02 (m, 1H), 3.81 (d, J=11.7 Hz, 1H), 3.72 (d, J=16.8 Hz, 1H), 3.68 (d, J=16.8 Hz, 1H), 3.64 (m, 1H), 3.37-3.29 (m, 4H), 2.79 (m, 1H), 2.72 (t, J=5.8 Hz, 4H), 2.44-2.33 (m, 6H), 2.30 (s, 3H), 2.26 (broad s, 2H), 1.59 (m, 2H), 1.50 (m, 2H), 1.43 (m, 2H), 1.36 (m, 2H), 1.11 (d, J=7.0 Hz, 3H), 1.10 (d, J=7.0 Hz, 3H).

EXAMPLE 2

Synthesis of 4-{4-[(1E)-4-(2,8-diazaspiro[4.5]dec-2-yl)but-1-en-1-yl]-2-methylbenzyl}-5-(propan-2-yl)-1H-pyrazol-3-yl beta-D-glucopyranoside

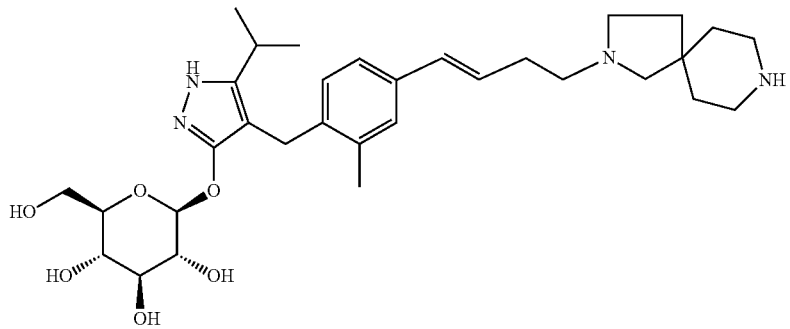 [SMILES: Cc1cc(/C=C/CCN2CCC3(CCNCC3)C2)ccc1Cc1c(O[C@@H]2O[C@H](CO)[C@@H](O)[C@H](O)[C@H]2O)n[nH]c1C(C)C]

The title compound is prepared essentially by the method of the first alternative synthesis of Example 1. MS (m/z): 584.7 (M+1), 582.8 (M−1).

EXAMPLE 3

Synthesis of 4-{4-[(1E)-4-(3,9-diazaspiro[5.5]undec-3-yl)but-1-en-1-yl]-2-methylbenzyl}-5-(propan-2-yl)-1H-pyrazol-3-yl beta-D-glucopyranoside

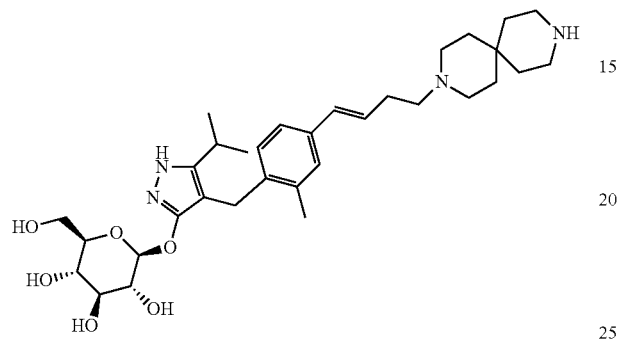

The title compound is prepared essentially by first treating the compound of Preparation 14 with HCl as discussed in Preparation 15 then treating the resulting hydrochloride salt with triethyl amine as discussed in the first alternative synthesis of Example 1. MS (m/z): 598.8, 599.8 (M+1), 596.8, 597.8 (M−1).

Scheme 3

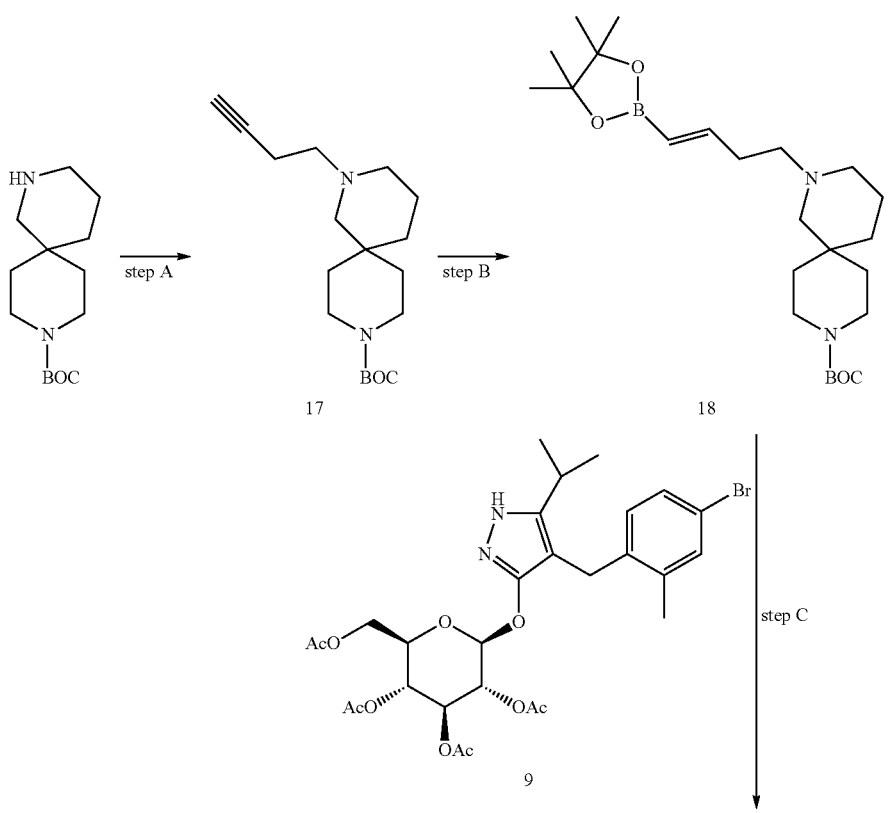

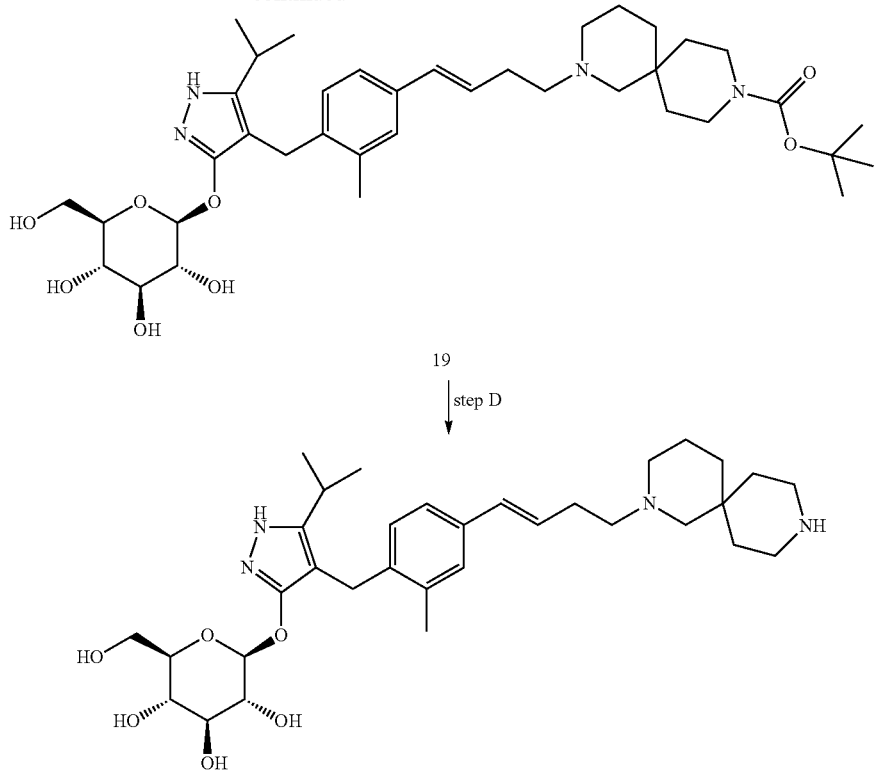

19 step D

Example 1

PREPARATION 17

Synthesis of tert-butyl 4-but-3-ynyl-4,9-diazaspiro[5.5]undecane-9-carboxylate

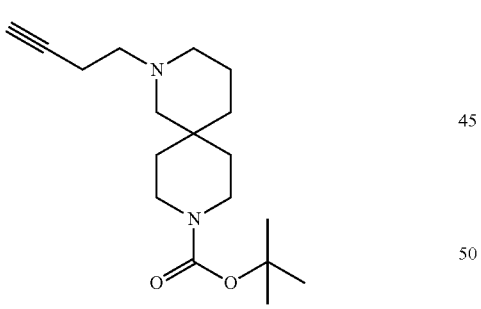

Scheme 3, step A: Cesium carbonate (46.66 g, 143.21 mmol) is added to a suspension of tert-butyl 4,9-diazaspiro[5.5]undecane-9-carboxylate hydrochloride (16.66 g, 57.28 mmoles) in acetonitrile (167 mL). The mixture is stirred for 10 minutes at ambient temperature then 4-bromobutyne (6.45 mL, 68.74 mmol) is added. The reaction is heated to reflux and stirred for 18 hours. The mixture is cooled and concentrated under reduced pressure. The residue is partitioned between water (200 mL) and ethyl acetate (150 mL). The phases are separated and the aqueous layer is extracted with ethyl acetate (100 mL). The combined organic layers are washed with water (200 mL), then brine (150 mL), dried over MgSO$_4$, filtered, and concentrated under reduced pressure to give the title compound (17.2 g, 98% yield). $^1$H NMR (300.11 MHz, CDCl$_3$): δ 3.43-3.31 (m, 4H), 2.53-2.48 (m, 2H), 2.37-2.29 (m, 4H), 2.20 (s, 2H), 1.94 (t, J=2.6 Hz, 1H), 1.44 (s, 17H).

PREPARATION 18

Synthesis of tert-butyl 4-[(E)-4-(4,4,5,5-tetramethyl-1,3,2-dioxaborolan-2-yl)but-3-enyl]-4,9-diazaspiro[5.5]undecane-9-carboxylate

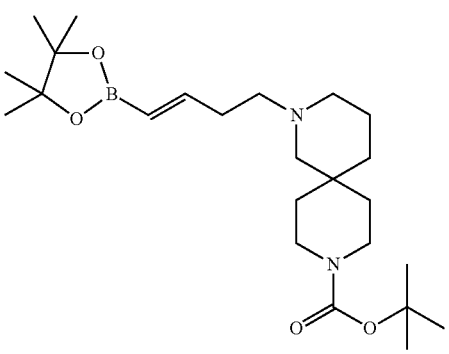 [SMILES: CC(C)(C)OC(=O)N1CCC2(CCCN(CC/C=C/B3OC(C)(C)C(C)(C)O3)C2)CC1]

Scheme 3, step B: Triethylamine (5.62 mmoles; 0.783 mL), 4,4,5,5-tetramethyl-1,3,2-dioxaborolane (8.56 mL, 59.0 mmol) and zirconocene chloride (1.45 g, 5.62 mmoles) are added to tert-butyl 4-but-3-ynyl-4,9-diazaspiro[5.5]undecane-9-carboxylate (17.21 g, 56.16 mmoles). The resulting mixture is heated to 65° C. for 3.5 hours. The mixture is cooled and dissolved in dichloromethane (150 mL). The resulting solution is passed through a ~4 cm thick pad of silica gel, eluting with dichloromethane (2×200 mL). The filtrate is concentrated under reduced pressure to give the title compound (21.2 g, 87% yield). $^1$H NMR (300.11 MHz, CDCl$_3$): δ 6.65-6.55 (m, 1H), 5.49-5.43 (m, 1H), 3.42-3.29 (m, 4H), 2.40-2.27 (m, 6H), 2.25-2.08 (m, 2H), 1.70-1.13 (m, 29H).

PREPARATION 19

Synthesis of tert-butyl 2-{(3E)-4-[3-methyl-4-({5-(propan-2-yl)-3-beta-D-glucopyranosyl)oxy]-1H-pyrazol-4-yl}methyl)phenyl]but-3-en-1-yl}-2,9-diazaspiro[5.5]undecane-9-carboxylate

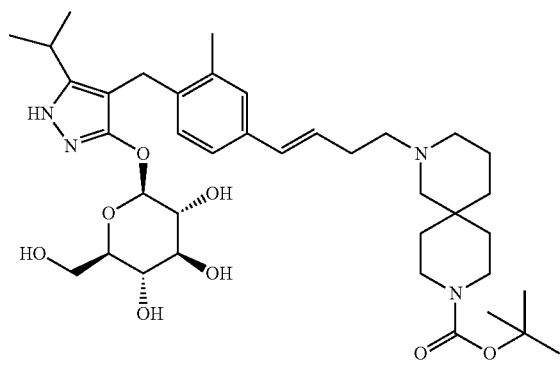 [SMILES: Cc1cc(/C=C/CCN2CCCC3(CCN(C(=O)OC(C)(C)C)CC3)C2)ccc1Cc1c(O[C@@H]2O[C@H](CO)[C@@H](O)[C@H](O)[C@H]2O)n[nH]c1C(C)C]

Scheme 3, step C: A solution of 4-(4-bromo-2-methylbenzyl)-5-(propan-2-yl)-1H-pyrazol-3-yl2,3,4,6-tetra-O-acetyl-beta-D-glucopyranoside (20 g, 31.3 mmol), tert-butyl 4-[(E)-4-(4,4,5,5-tetramethyl-1,3,2-dioxaborolan-2-yl)but-3-enyl]-4,9-diazaspiro[5.5]undecane-9-carboxylate (16.3 g, 37.5 mmol) and potassium carbonate (12.97 g, 93.82 mmol) in tetrahydrofuran (200 mL) and water (40 mL) is degassed for 15 min by bubbling nitrogen gas through it. Pd(OAc)$_2$ (140 mg, 625 mmol) and 2-dicyclohexylphosphino-2',4',6'-tri-1-propyl-1,1'-biphenyl (0.596 g, 1.25 mmol) are added and the reaction is heated to reflux for 16 h. The solution is cooled to ambient temperature and methanol (200 mL) is added. After 30 minutes the solvent is removed under reduced pressure. The mixture is partitioned between ethyl acetate (500 mL) and brine (500 ml) adding aqueous MgSO$_4$ (1M; 500 ml) to aid the phase separation. The layers are separated and the organic layer is dried over MgSO$_4$ and filtered through a 10 cm pad of silica gel, eluting with ethyl acetate (~1.5 L). The filtrate is discarded and the silica pad is flushed with 5% MeOH in THF (2 L). The methanolic filtrate is concentrated under reduced pressure to give the title compound (20.1 g, 92%).

MS (m/z): 699 (M+1).

Second Alternative Synthesis of Example 1

Second alternative synthesis of 4-{4-[(1E)-4-(2,9-diazaspiro[5.5]undec-2-yl)but-1-en-1-yl]-2-methylbenzyl}-5-(propan-2-yl)-1H-pyrazol-3-yl beta-D-glucopyranoside

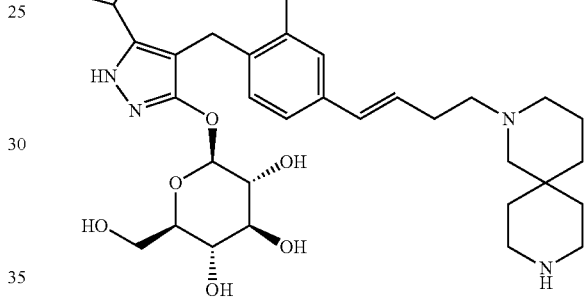

Scheme 3, step D: Trifluoroacetic acid (32.2 mL; 0.426 mol) is added to a solution of tert-butyl 2-{(3E)-4-[3-methyl-4-({5-(propan-2-yl)-3-beta-D-glucopyranosyl)oxy]-1H-pyrazol-4-yl}methyl)phenyl]but-3-en-1-yl}-2,9-diazaspiro[5.5]undecane-9-carboxylate (14.87 g; 21.28 mmol) in dichloromethane (149 mL) cooled in iced water. The solution is allowed to warm to room temperature. After 30 minutes, the mixture is slowly added to ammonia in MeOH (2M; 300 mL), applying cooling as necessary to maintain a constant temperature. The solution is stirred at room temperature for 15 min. The mixture is concentrated under reduced pressure and the residue is purified using SCX-2 resin. The basic filtrate is concentrated under reduced pressure and the residue is triturated/sonicated in ethyl acetate, filtered and dried. The resulting solid is dissolved in MeOH (200 ml) and concentrated in vacuo. This is repeated several times give the title compound (12.22 g, yield 96%). MS (m/z): 599 (M+1).

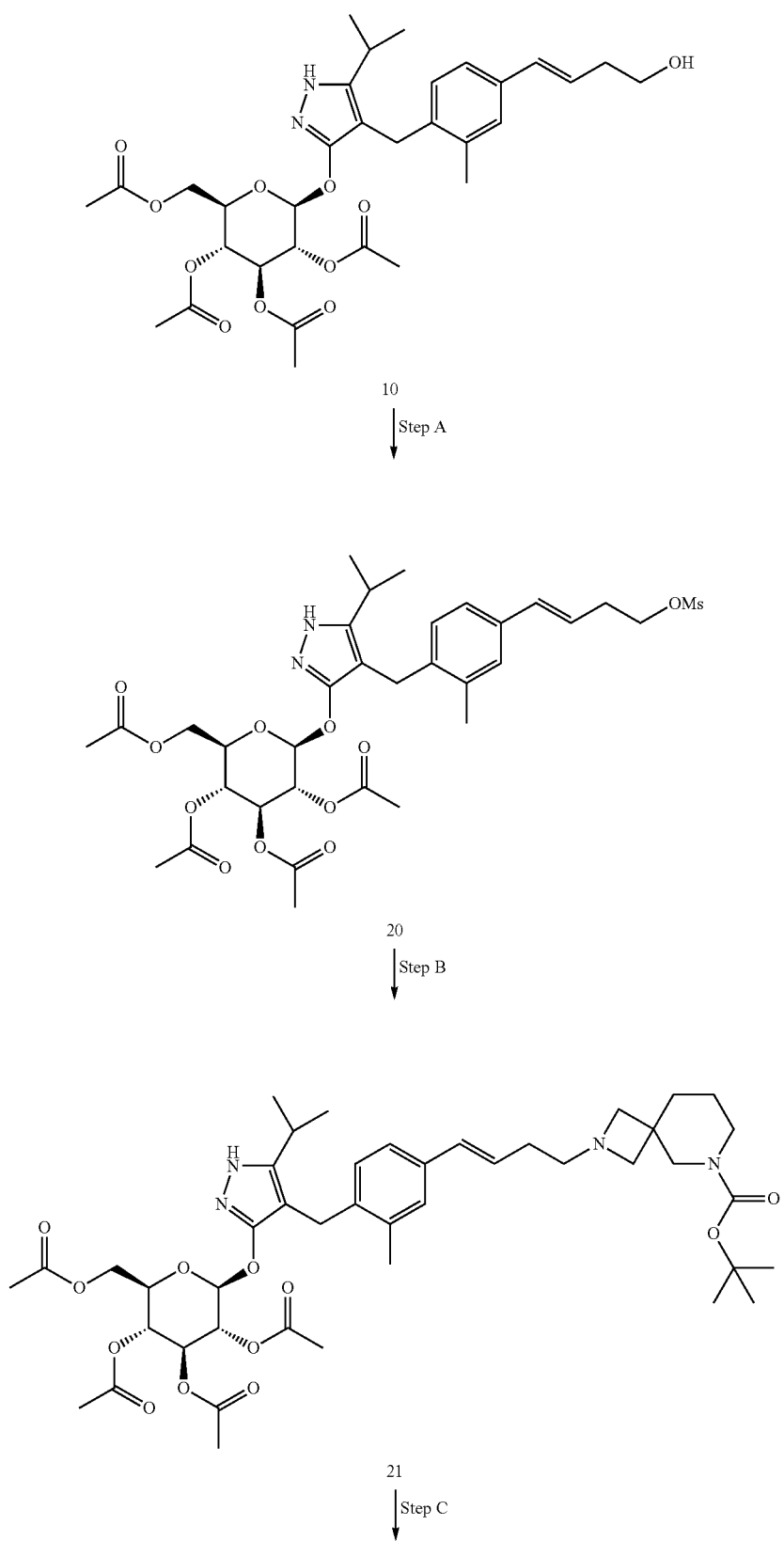

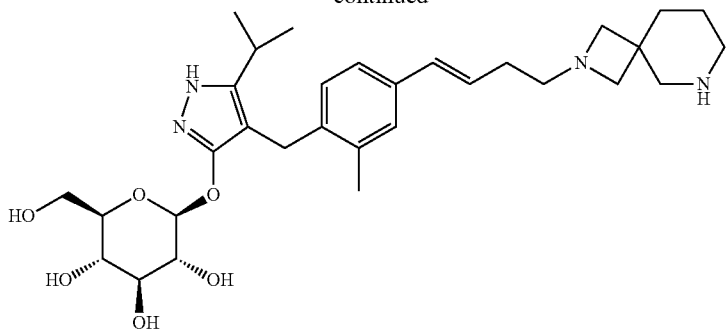

Example 4

PREPARATION 20

Synthesis of (3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl methanesulfonate

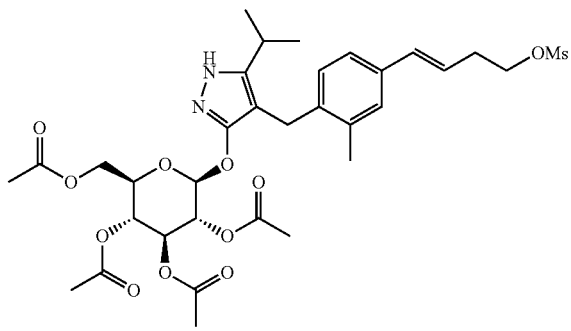 [SMILES: CC(=O)OC[C@H]1O[C@@H](Oc2n[nH]c(C(C)C)c2Cc2ccc(/C=C/CCOS(C)(=O)=O)cc2C)[C@H](OC(C)=O)[C@@H](OC(C)=O)[C@@H]1OC(C)=O]

Scheme 4, step A. Add methanesulfonyl chloride (0.54 mL, 7 mmol) to a solution of 4-{4-[(1E)-4-hydroxybut-1-en-1-yl]-2-methylbenzyl}-5-(propan-2-yl)-1H-pyrazol-3-yl2,3,4,6-tetra-O-acetyl-beta-D-glucopyranoside (3.7, 5.87 mmol) in dichloromethane (15 mL) and triethylamine (4 mL, 29 mmol) at 0° C. After refluxing at room temperature for 30 min, concentrate to remove the solvent under the reduced pressure. Purify residue by flash chromatography to yield the title compound (2.9 g, 4.1 mmol).

MS (m/z): 708.5 (M+1), 706.5 (M−1).

PREPARATION 21

Synthesis of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,6-diazaspiro[3.5]nonane-6-carboxylate

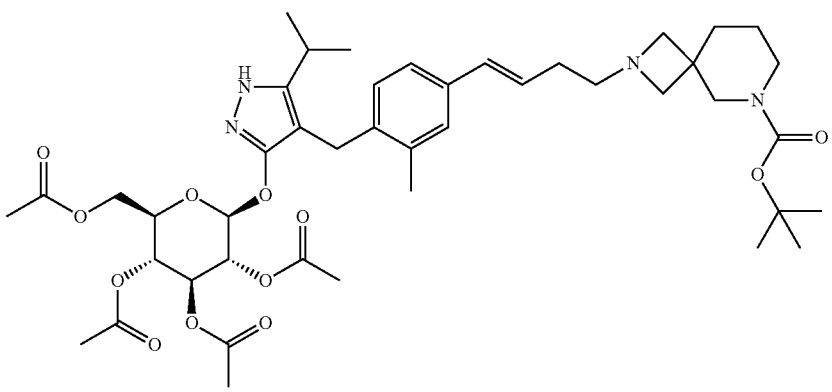 [SMILES: CC(=O)OC[C@H]1O[C@@H](Oc2n[nH]c(C(C)C)c2Cc2ccc(/C=C/CCN3CC4(CCCN(C(=O)OC(C)(C)C)C4)C3)cc2C)[C@H](OC(C)=O)[C@@H](OC(C)=O)[C@@H]1OC(C)=O]

Scheme 4, step B. Add diisopropylethylamine (0.2 mL, 1.1 mmol) to a solution of (3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl methanesulfonate (200 mg, 0.28 mmol) and tert-butyl 2,6-diazaspiro[3.5]nonane-6-carboxylate (77 mg, 0.34 mmol) in acetonitrile (3 mL). Heat the mixture at 80° C. for overnight. Concentrate under reduced pressure and purify residue by flash chromatography to yield the title compound (127 mg, 0.15 mmol). MS (m/z): 838.8, 839.6 (M+1), 836.8, 837.6 (M−1).

PREPARATION 22

Synthesis of tert-butyl 2-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,7-diazaspiro[3.5]nonane-7-carboxylate

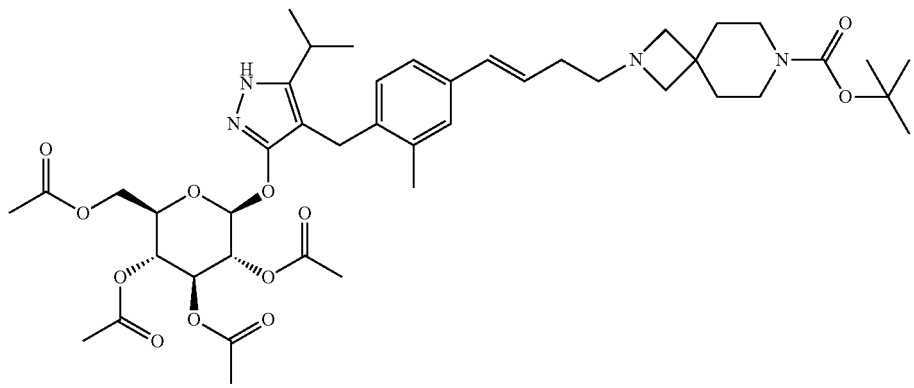 [SMILES: CC(=O)OC[C@H]1O[C@@H](Oc2n[nH]c(C(C)C)c2Cc2ccc(/C=C/CCN3CC4(CCN(C(=O)OC(C)(C)C)CC4)C3)cc2C)[C@H](OC(C)=O)[C@@H](OC(C)=O)[C@@H]1OC(C)=O]

The title compound is prepared essentially as the method of Preparation 21.

MS (m/z): 838.8, 839.6 (M+1), 836.8, 837.6 (M−1).

PREPARATION 23

Synthesis of tert-butyl 7-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-2,7-diazaspiro[3.5]nonane-2-carboxylate

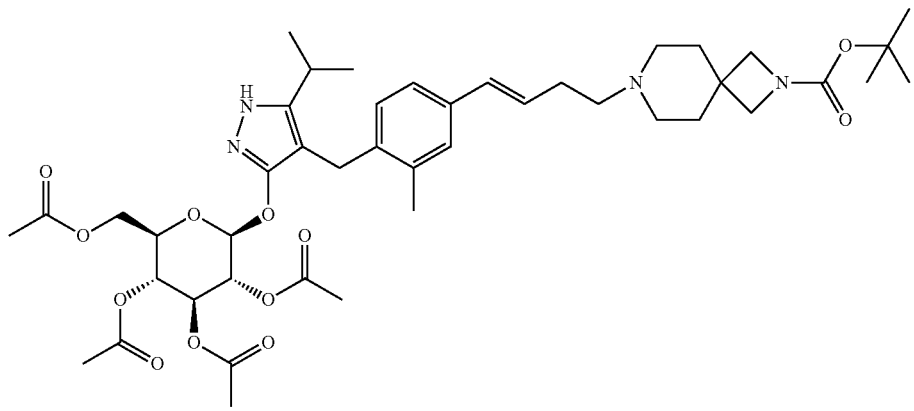 [SMILES: CC(=O)OC[C@H]1O[C@@H](Oc2n[nH]c(C(C)C)c2Cc2ccc(/C=C/CCN3CCC4(CC3)CN(C(=O)OC(C)(C)C)C4)cc2C)[C@H](OC(C)=O)[C@@H](OC(C)=O)[C@@H]1OC(C)=O]

The title compound is prepared essentially as the method of Preparation 21.

MS (m/z): 838.8, 839.6 (M+1), 836.8, 837.6 (M−1).

PREPARATION 24

Synthesis of tert-butyl 1-{(3E)-4-[3-methyl-4-({5-(propan-2-yl)-3-[(2,3,4,6-tetra-O-acetyl-beta-D-glucopyranosyl)oxy]-1H-pyrazol-4-yl}methyl)phenyl]but-3-en-1-yl}-1,8-diazaspiro[4.5]decane-8-carboxylate The title compound is prepared essentially as the method of Preparation 21.

MS (m/z): 852.8, 853.6 (M+1), 850.8, 852.8 (M−1).

PREPARATION 25

Synthesis of tert-butyl 8-{(3E)-4-[3-methyl-4-({5-(propan-2-yl)-3-[(2,3,4,6-tetra-O-acetyl-beta-d-glucopyranosyl)oxy]-1H-pyrazol-4-yl}methyl)phenyl]but-3-en-1-yl}-2,8-diazaspiro[4.5]decane-2-carboxylate The title compound is prepared essentially as the method of Preparation 21.

MS (m/z): 852.8, 853.6 (M+1), 850.8, 851.6 (M−1).

EXAMPLE 4

Synthesis of 4-{4-[(1E)-4-(2,6-diazaspiro[3.5]non-2-yl)but-1-en-1-yl]-2-methylbenzyl}-5-(propan-2-yl)-1H-pyrazol-3-yl beta-D-glucopyranoside

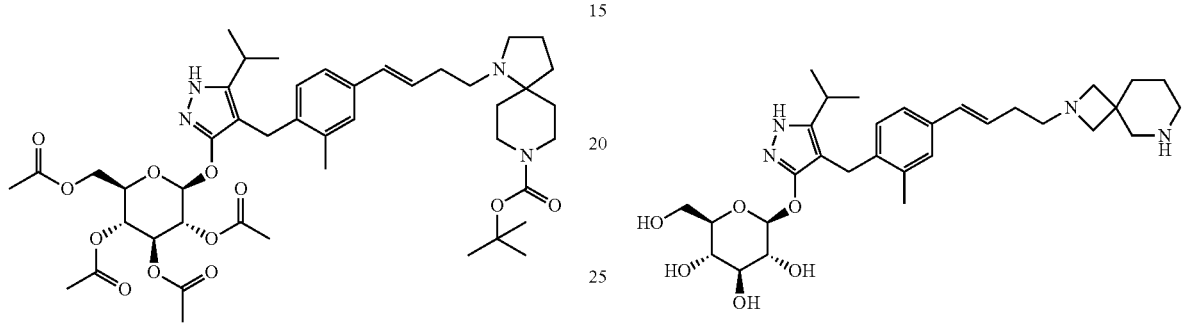

Scheme 4, step C. Add 4.0 M HCl/1,4-dioxane (1.5 mL, 1.5 mmol) to a solution of tert-butyl 2-{(3E)-4-[3-methyl-4-({5-(propan-2-yl)-3-[(2,3,4,6-tetra-O-acetyl-beta-D-glucopyranosyl)oxy]-1 h-pyrazol-4-yl}methyl)phenyl]but-3-en-1-yl}-2,6-diazaspiro[3.5]nonane-6-carboxylate in dichloromethane (2 mL) and stir at rt for 4.0 h. Concentrate the mixture under the reduced pressure to a foamy solid. Treat the solid with 2.0 M ammonia in MeOH (2 mL) overnight. After 18 hours at room temperature, concentrate to remove the solvent under reduced pressure. The resulting residue is purified by preparative HPLC method: high pH, 19% B for 3 min, 19-34 B % for 5 min @ 85 mL/min using a 30×75 mm, 5 um C18XBridge ODB column, solvent A—H₂O w NH₄HCO₃ @ pH 10, solvent B-MeCN to yield the title compound as solid (47 mg, 0.08 mmol). MS (m/z): 570.8, 571.8 (M+1), 568.7, 569.8 (M−1).

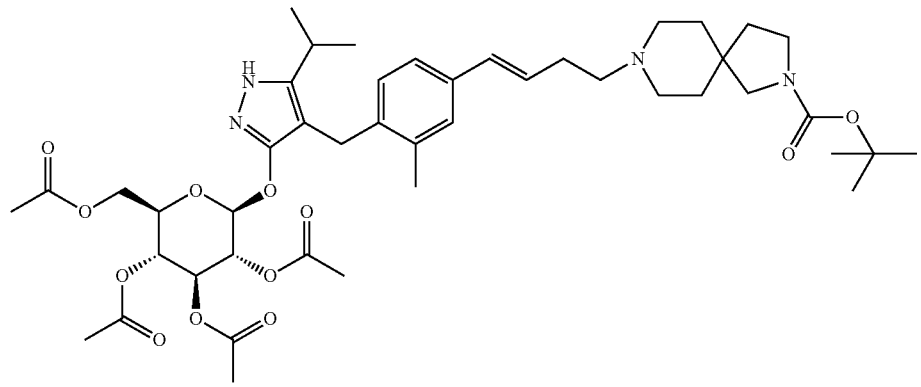 [SMILES: CC(=O)OC[C@H]1O[C@@H](Oc2n[nH]c(C(C)C)c2Cc2ccc(/C=C/CCN3CCC4(CC3)CCN(C(=O)OC(C)(C)C)C4)cc2C)[C@H](OC(C)=O)[C@@H](OC(C)=O)[C@@H]1OC(C)=O]

EXAMPLE 5

Synthesis of 4-{4-[(1E)-4-(2,7-diazaspiro[3.5]non-2-yl)but-1-en-1-yl]-2-methylbenzyl}-5-(propan-2-yl)-1H-pyrazol-3-yl beta-D-glucopyranoside

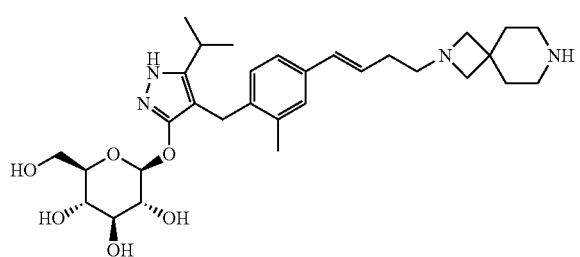 [SMILES: Cc1cc(/C=C/CCN2CC3(CCNCC3)C2)ccc1Cc1c(O[C@@H]2O[C@H](CO)[C@@H](O)[C@H](O)[C@H]2O)n[nH]c1C(C)C]

The title compound is prepared essentially by the method of Example 4.

MS (m/z): 570.8, 571.8 (M+1), 568.7, 569.8 (M−1).

EXAMPLE 6

Synthesis of 4-{4-[(1E)-4-(2,7-diazaspiro[3.5]non-7-yl)but-1-en-1-yl]-2-methylbenzyl}-5-(propan-2-yl)-1H-pyrazol-3-yl beta-D-glucopyranoside trifluoroacetate (1:2)

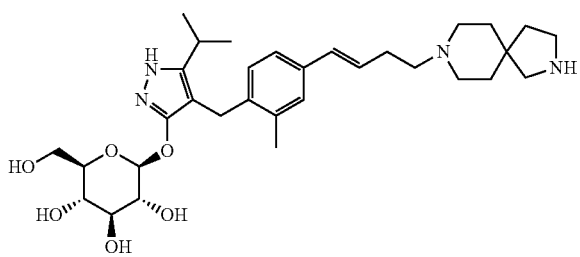 [SMILES: Cc1cc(/C=C/CCN2CCC3(CCNC3)CC2)ccc1Cc1c(O[C@@H]2O[C@H](CO)[C@@H](O)[C@H](O)[C@H]2O)n[nH]c1C(C)C]

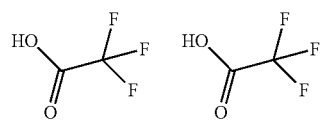

The title compound is prepared essentially by the method of Example 4 with the final compound being purified by low pH preparative HPLC method (low pH, 16% B for 3 min, 16-33 B % for 5 min @ 85 mL/min using a 30×75 mm, 5 um C18XBridge ODB column, solvent A—H$_2$O w 0.1% TFA, solvent B-MeCN w 0.1% TFA).

MS (m/z): 570.8, 571.8 (M+1), 568.7, 569.8 (M−1).

EXAMPLE 7

Synthesis of 4-{4-[(1E)-4-(1,8-diazaspiro[4.5]dec-1-yl)but-1-en-1-yl]-2-methylbenzyl}-5-(propan-2-yl)-1H-pyrazol-3-yl beta-d-glucopyranoside

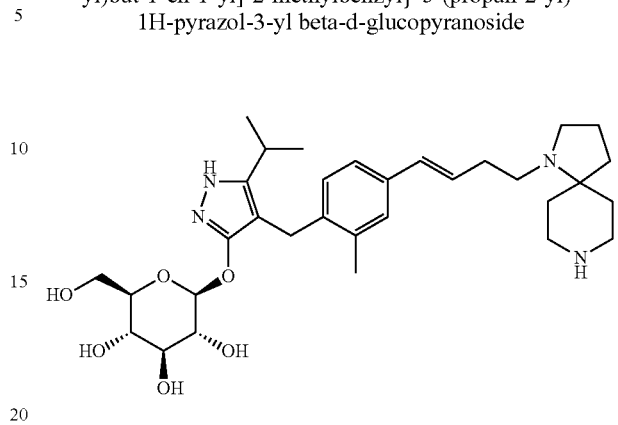

The title compound is prepared essentially by the method of Example 4.

MS (m/z): 584.7, 585.8 (M+1), 582.8, 583.8 (M−1).

EXAMPLE 8

Synthesis of 4-{4-[(1E)-4-(2,8-diazaspiro[4.5]dec-8-yl)but-1-en-1-yl]-2-methylbenzyl}-5-(propan-2-yl)-1H-pyrazol-3-yl beta-D-glucopyranoside

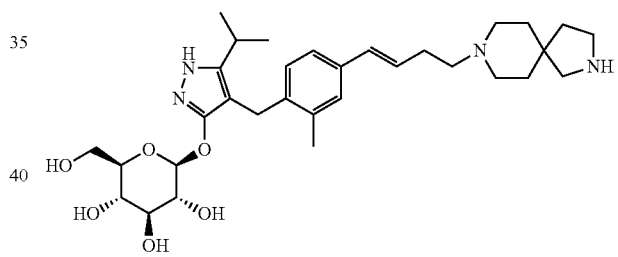

The title compound is prepared essentially by the method of Example 4.

MS (m/z): 584.7, 585.8 (M+1), 582.8, 583.8 (M−1).

Sodium-Dependent Glucose Transporter 1 (SGLT1) and SGLT2 Assays

The cDNA encoding human SGLT1 (slc5a1, NM_000343), human SGLT2 (slc5a2, NM_003041) and mouse SGLT1 (slc5a1, NM_019810.4) are purchased from Openbiosystems, Invitrogen and Openbiosystems, respectively. The cDNA is cloned into pcDNA3.1+ for mammalian expression and is stably transfected into Chinese hamster ovary (CHO)-K1 cells using standard mammalian transfection procedures. An SGLT-expressing sub-clone of each over-expressing cell line is selected based on resistance to neomycin (Geneticin, Invitrogen) and activity in the $^{14}$C-α-methyl-D-glucopyranoside ($^{14}$C-AMG) uptake assay (see below). Stable SGLT-expressing cells are maintained using standard cell culture techniques.

The SGLT activity is measured as sodium-dependent $^{14}$C-AMG uptake in the above cell lines described as follows. One hundred µL of culture medium containing 30,000 cells are seeded to each well of a 96-well BioCoat poly-D-lysine plate (Becton Dickson) and cultured at 37° C. overnight. The culture medium is aspirated and cells are washed twice with 200 µL of Reaction Buffer (140 mM NaCl, 2 mM KCl, 1 mM $CaCl_2$, $MgCl_2$, and 14 mM N-2-hydroethylpiperrazine-N'-2-ethanesulfonic acid (Hepes), pH 7.5). The excess buffer is tapped out onto paper towels. Thirty-five µL of Reaction Buffer are added to each well. Five µL of a 10% dimethylsufoxide (DMSO) in Reaction Buffer containing varying concentrations of test compound or no compound as a control, is dispensed into the each well. The reaction is initiated by adding 10 µL of $^{14}C$-AMG in Reaction Buffer to make a final concentration of 4 µM. The plate is incubated at 37° C. for 125 minutes. The reaction is terminated by aspirating off Reaction Buffer and then washed three times with 200 µL of ice cold Reaction Buffer. Manual aspiration is applied to ensure the complete removal of Reaction Buffer. Ten µL of 0.1 N NaOH is added to each well and then 100 µL of Supermix scintillation cocktail (PerkinElmer) is added. After mixing, the scintillation signal in the plate is counted in a MicroBeta (PerkinElmer). A ten-dose response curve is fitted to an empirical four-parameter model using ActivityBase (ID Business Solution) to determine the inhibitor concentration at half-maximal inhibition ($IC_{50}$). The compounds of Examples 1-8 herein are tested essentially as described above and exhibit an $IC_{50}$ value for SGLT1 of lower than about 500 nM.

More specifically, the data in table 1 demonstrate that the compound of Example 1 inhibits human and mouse SGLT1 in vitro, and is more potent at human and mouse SGLT1 than at human SGLT2 in vitro.

Glucose Lowering Effects in Oral Glucose Tolerance Test (OGTT)

The test compound is formulated by adding a vehicle of 1% hydroxyethylcellulose, 0.25% Tween® 80 w/antifoam 0.05% to preweighed test compound to make a 1 mg/ml solution. The mixture is probe sonicated for approximately 30 seconds. The resulting solution is used as a stock solution from which the lower concentration dose solutions are prepared by dilution with the vehicle.

Single housed C57Bl/6 mice are fasted overnight by removing access to food the late afternoon before test day. The following morning, the mice are weighed and a single fasting blood sample is taken by tail snip to measure glucose by glucometer (Roche AccuChek). Study groups (n=5) are determined based on fasted blood glucose and comprise preferably animals in the range of 80-100 mg/dl glucose.

After grouping, the first mouse is orally gavaged with 10 ml/kg test compound preparation and a timer started. Each subsequent animal is dosed a minute and a half apart. Three hours after the first compound treatment is started, a baseline blood sample is taken for measuring glucose (from the first animal, via tail snip). The animal is then immediately given an oral dose of 50% dextrose (Hospira) at 3 g/kg. Blood samples are taken for glucose, exactly a minute and half apart, by tail vein so that blood is collected in each animal at 20, 40, 60 and 120 minutes after the dextrose dose.

TABLE 1

In vitro potency of Example 1 against SGLT1 and SGLT2

| Test Compound | Human SGLT1 $IC_{50}$, nM | Human SGLT2 $IC_{50}$, nM | Mouse SGLT1 $IC_{50}$, nM |
|---|---|---|---|
| Example 1 | 26 ± 20 (n = 10) | 6100 ± 1200 (n = 10) | 10 ± 2 (n = 9) |

TABLE 2

Glucose lowering effects in OGTT.
Oral Glucose Tolerance Test Results Mean ± SE

| | Vehicle | Example 1 0.3 mg/kg | Example 1 1 mg/kg | Example 1 3 mg/kg | Example 1 10 mg/kg |
|---|---|---|---|---|---|
| 2 way ANOVA/Bonferroni's *p < 0.05, **p < 0.01, ***p < 0.001 compared to vehicle | | | | | |
| Glucose (mg/dl) | | | | | |
| 0 Minute | 84 ± 8.4 | 78 ± 4.2 | 76 ± 3.3 | 72 ± 2.6 | 78 ± 5.4 |
| 20 Minute | 268 ± 49.3 | 185 ± 13.7*** | 147 ± 8.3*** | 133 ± 7.1*** | 124 ± 1.2*** |
| 40 Minute | 192 ± 26.8 | 197 ± 14.7 | 171 ± 11.1 | 150 ± 7.5 | 137 ± 5.4** |
| 60 Minute | 139 ± 6.2 | 164 ± 6.3 | 162 ± 5.8 | 155 ± 7.2 | 138 ± 6.1 |
| 120 Minute | 105 ± 5.1 | 121 ± 11.8 | 109 ± 7.3 | 115 ± 10 | 114 ± 4.3 |
| 1 way ANOVA/Dunnett's *p < 0.05, **p < 0.01, ***p < 0.001 compared to vehicle | | | | | |
| Baseline Adjusted AUC | 6408 ± 1500 | 5400 ± 519 | 4158 ± 374 | 3606 ± 421* | 2693 ± 309** |
| Glucose (mg/dl) | | | | | |
| Glucose Cmax | 268 ± 49.3 | 199 ± 14.1 | 174 ± 9.38** | 161 ± 5.00** | 141 ± 5.67** |
| Time (minutes) | | | | | |
| Glucose Tmax | 20 ± 0 | 32 ± 5 | 48 ± 5 | 64 ± 13** | 44 ± 7 |

As shown above in table 2, the compound of example 1 delivers a dose dependent decrease in the glucose excursion following an oral bolus of 50% dextrose (Hospira®) in the normal glycemic C57Bl/6 mouse. Example 1 also demonstrates a dose dependent decrease in baseline adjusted glucose area under the curve (AUC) during an OGTT. In addition, example 1 dose dependently decreases the average maximum concentration of plasma glucose (Cmax) during the OGTT while increasing the average time that it takes for glucose to reach maximum concentration (Tmax).

Glucose Values in a Mixed Meal Tolerance Test in Male Rats with Streptozotocin Induced Diabetes Rats which have been administered streptozotocin (STZ) develop diabetes mellitus. Agents which modulate glucose levels in these animals are believed to be useful in the treatment of diabetes in humans.

The test compound is formulated by adding a vehicle of 1% hydroxyethylcellulose (HEC), 0.25% Tween® 80 w/antifoam 0.05% to preweighed test compound to make a 2.5 mg/ml solution. The mixture is probe sonicated for approximately 30 seconds. The resulting solution is used as a stock solution, from which the lower concentration dose solutions are prepared by dilution with the vehicle. STZ, 45 mg/kg, is formulated by dissolving in 0.1M Citrate buffer in 3 ml aliquots and stored in the dark on ice, when not being administered. A high fat content mixed meal (Bio-Serv® Rodent Diet F3282 High Fat) comprising Fat Calories (60%), Carbohydrate Calories (26%) and Protein Calories (15%) is utilized. Single housed Sprague Dawley rats are allowed to acclimate for a period of 3 to 7 days.

In an effort to ensure that the animals have not recently fed, STZ is administered in the afternoon, approximately six hours into the light cycle (lights on 6 am, lights off 6 pm). The animals are anesthetized with isoflurane and STZ is delivered via tail vein injection. Once animals regain consciousness, they are returned to housing and allowed to recover for 7 days.

On the two days immediately prior to the meal tolerance test (MTT) all rats are given a small amount (2-4 g) of the F3282 diet, so they became acclimated to it prior to receiving it during the experiment. On the evening before the experiment, the rats are moved into clean cages and their food is removed. The following morning animals are weighed and a blood sample is taken by tail snip for glucose measurement (Abbott AlphaTrak glucometers: code 29). Animals are grouped n=6 based on fasted body weight and glucose. Thirty minutes after the test compound is orally administered, two glucose measurements are collected. Then a five gram pellet of Bio-Serv® diet 3282 is given. After 20 minutes remaining food is taken away and weighed. Blood samples are taken at 20, 40, 60 and 120 minutes for glucose measurement.

TABLE 3

Glucose values in a mixed MTT in male rats with STZ-induced diabetes.

| Treatment | Dose | Glucose Values (mg/dl) Groups n = 5-6, Mean ± SE | | | | | |
|---|---|---|---|---|---|---|---|
| | | 0 min. | 20 min. | 40 min. | 60 min. | 120 min. | Baseline Adjusted AUC |
| Vehicle | | 113.6 ± 12.6 | 297.2 ± 26.6 | 427.6 ± 41 | 452.2 ± 37.3 | 544.7 ± 50.1 | 36429 ± 3155 |
| Example 1 | 10 mg/kg | 139 ± 16.1 | 221.2 ± 26.3 | 268.7 ± 29* | 330 ± 36.7 | 490.8 ± 39.2 | 22432 ± 2234* |
| Example 1 | 30 mg/kg | 137.4 ± 26.9 | 195.4 ± 44.8 | 232 ± 52.2** | 263.9 ± 62.2* | 355.3 ± 73.2* | 14649 ± 3673** |
| Acarbose | 60 mg/kg | 124 ± 16.9 | 181 ± 22.8 | 301.3 ± 51.2 | 371.5 ± 63.9 | 433.7 ± 83 | 23877 ± 4649* |

2 way ANOVA/ Bonferroni's
*p < 0.05,
**p < 0.01

As shown in table 3 above, the compound of example 1 significantly and dose dependently decreases glucose in the MTT compared to the vehicle controls. Acarbose did not significantly decrease glucose compared to controls at any time point. Further, there is a dose dependent decrease in glucose baseline adjusted AUCs associated with Example 1 treatment. Acarbose significantly decreases the glucose AUCs to levels similar to that of Example 1 at 10 mg/kg. Table 3 demonstrates that the compound of example 1 modulates glucose levels in the male rat.

We claim:
1. A compound of the formula:

[Structure of compound]

wherein X represents the following:

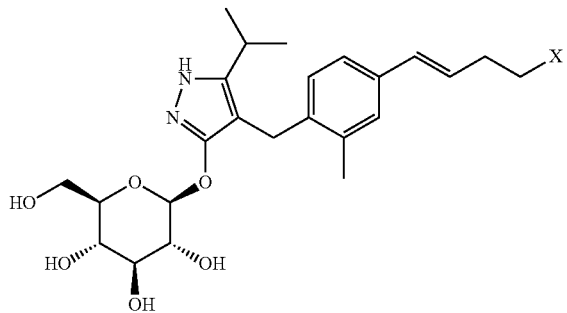

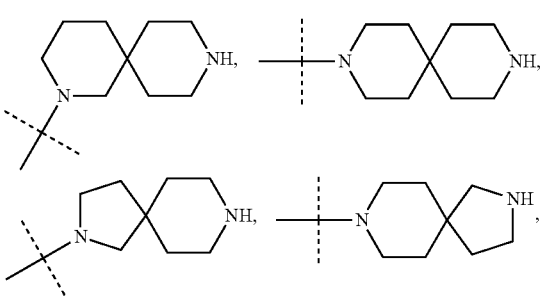

-continued

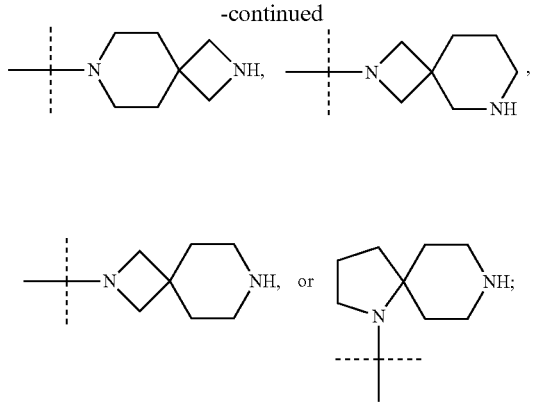

or a pharmaceutically acceptable salt thereof.

2. The compound or salt according to claim 1 which is:

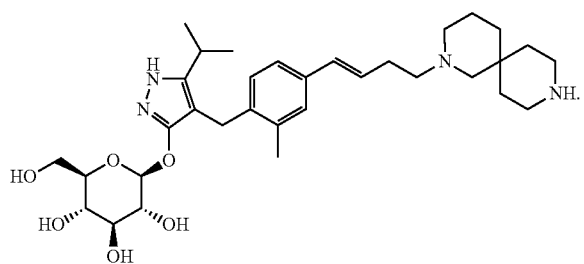 [SMILES: Cc1cc(/C=C/CCN2CCCC3(CCNCC3)C2)ccc1Cc1c(O[C@@H]2O[C@H](CO)[C@@H](O)[C@H](O)[C@H]2O)n[nH]c1C(C)C]

3. The compound according to claim 2 which is:

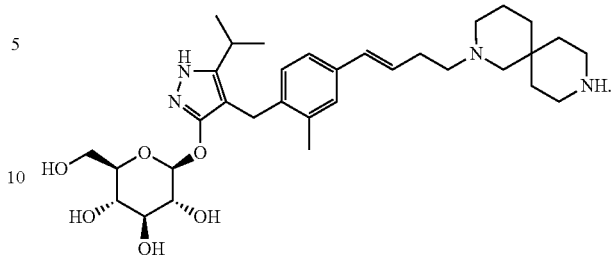

4. A method of treating diabetes in a patient comprising administering to a patient in need of such treatment an effective amount of a compound, or pharmaceutically acceptable salt thereof, according to claim 1.

5. A method of treating type 1 diabetes in a patient comprising administering to a patient in need of such treatment an effective amount of a compound, or pharmaceutically acceptable salt thereof, according to claim 1.

6. A method of treating type 2 diabetes in a patient comprising administering to a patient in need of such treatment an effective amount of a compound, or pharmaceutically acceptable salt thereof, according to claim 1.

7. A pharmaceutical composition comprising a compound or a pharmaceutically acceptable salt thereof according to claim 1 in combination with one or more pharmaceutically acceptable carriers, diluents, or excipients.

8. The pharmaceutical composition according to claim 7, further comprising one or more other therapeutic agents.

* * * * *